US012575927B2

(12) United States Patent
Nir et al.

(10) Patent No.: US 12,575,927 B2
(45) Date of Patent: Mar. 17, 2026

(54) PROSTHETIC HEART VALVES

(71) Applicant: Edwards Lifesciences Corporation, Irvine, CA (US)

(72) Inventors: Noam Nir, Pardes-Hanna (IL); Michael Bukin, Pardes Hanna (IL); Ziv Yohanan, Kfar Hahoresh (IL); Tamir S. Levi, Zikhron Yaakov (IL); Elena Sherman, Pardes Hana (IL)

(73) Assignee: Edwards Lifesciences Corporation, Irvine, CA (US)

( * ) Notice: Subject to any disclaimer, the term of this patent is extended or adjusted under 35 U.S.C. 154(b) by 1007 days.

(21) Appl. No.: 17/669,138

(22) Filed: Feb. 10, 2022

(65) Prior Publication Data

US 2022/0160505 A1     May 26, 2022

Related U.S. Application Data

(63) Continuation of application No. PCT/US2020/045577, filed on Aug. 10, 2020.

(Continued)

(51) Int. Cl.
*A61F 2/24*          (2006.01)

(52) U.S. Cl.
CPC .... *A61F 2/2418* (2013.01); *A61F 2220/0075* (2013.01); *A61F 2250/001* (2013.01); *A61F 2250/0036* (2013.01)

(58) Field of Classification Search
None
See application file for complete search history.

(56) References Cited

U.S. PATENT DOCUMENTS 3,409,013 A     11/1968  Berry
3,548,417 A     12/1970  Kisher
(Continued)

FOREIGN PATENT DOCUMENTS

CN        108125732      *  6/2018  ........... A61F 2/2412
DE          0144167  C       9/1903
(Continued)

OTHER PUBLICATIONS

H.R. Andersen, et al. "Transluminal Implantation of Artificial Heart Valve. Description of a New Expandable Aortic Valve and Initial Results with implantation by Catheter Technique in Closed Chest Pig," European Heart Journal, No. 13. pp. 704-708. 1992.
(Continued)

*Primary Examiner* — Melanie R Tyson
(74) *Attorney, Agent, or Firm* — Klarquist Sparkman, LLP

(57)                    ABSTRACT
Disclosed are techniques for construction of prosthetic heart valves, particularly techniques for attachment of scalloped edges of valvular leaflets to struts of mechanical frames using sutures and/or other materials as intermediate coupling members. In some embodiments, the scalloped edges of the leaflets are coupled to the segments of the struts of the frame via suture loops that are oriented transverse to the scalloped edges of the leaflets. In some embodiments, central portions of scallop line segments are attached to the scalloped edges of the leaflets and are not attached to the frame. In some embodiments, strut segments are tapered to limit translation of suture loops. In some embodiments, a cloth strip couples the scalloped edges of the leaflets to frame struts. In some embodiments, the scalloped edge is attached to adjacent segments of intersecting struts via sliding suture loops, where the adjacent segments join at a common pivot joint.

20 Claims, 28 Drawing Sheets

Related U.S. Application Data

(60) Provisional application No. 62/885,556, filed on Aug. 12, 2019.

(56) References Cited

U.S. PATENT DOCUMENTS

| | | | |
|---|---|---|---|
| 3,587,115 A | 6/1971 | Shiley |
| 3,657,744 A | 4/1972 | Ersek |
| 3,671,979 A | 6/1972 | Moulopoulos |
| 3,714,671 A | 2/1973 | Edwards et al. |
| 3,755,823 A | 9/1973 | Hancock |
| 4,035,849 A | 7/1977 | Angell et al. |
| 4,056,854 A | 11/1977 | Boretos et al. |
| 4,106,129 A | 8/1978 | Carpentier et al. |
| 4,222,126 A | 9/1980 | Boretos et al. |
| 4,265,694 A | 5/1981 | Boretos et al. |
| 4,297,749 A | 11/1981 | Davis et al. |
| 4,339,831 A | 7/1982 | Johnson |
| 4,343,048 A | 8/1982 | Ross et al. |
| 4,345,340 A | 8/1982 | Rosen |
| 4,373,216 A | 2/1983 | Klawitter |
| 4,406,022 A | 9/1983 | Roy |
| 4,441,216 A | 4/1984 | Ionescu et al. |
| 4,470,157 A | 9/1984 | Love |
| 4,535,483 A | 8/1985 | Klawitter et al. |
| 4,574,803 A | 3/1986 | Storz |
| 4,592,340 A | 6/1986 | Boyles |
| 4,605,407 A | 8/1986 | Black et al. |
| 4,612,011 A | 9/1986 | Kautzky |
| 4,643,732 A | 2/1987 | Pietsch et al. |
| 4,655,771 A | 4/1987 | Wallsten |
| 4,692,164 A | 9/1987 | Dzemeshkevich et al. |
| 4,733,665 A | 3/1988 | Palmaz |
| 4,759,758 A | 7/1988 | Gabbay |
| 4,762,128 A | 8/1988 | Rosenbluth |
| 4,777,951 A | 10/1988 | Cribier et al. |
| 4,787,899 A | 11/1988 | Lazarus |
| 4,787,901 A | 11/1988 | Baykut |
| 4,796,629 A | 1/1989 | Grayzel |
| 4,820,299 A | 4/1989 | Philippe et al. |
| 4,829,990 A | 5/1989 | Thuroff et al. |
| 4,851,001 A | 7/1989 | Taheri |
| 4,856,516 A | 8/1989 | Hillstead |
| 4,878,495 A | 11/1989 | Grayzel |
| 4,878,906 A | 11/1989 | Lindemann et al. |
| 4,883,458 A | 11/1989 | Shiber |
| 4,922,905 A | 5/1990 | Strecker |
| 4,966,604 A | 10/1990 | Reiss |
| 4,979,939 A | 12/1990 | Shiber |
| 4,986,830 A | 1/1991 | Owens et al. |
| 4,994,077 A | 2/1991 | Dobben |
| 5,007,896 A | 4/1991 | Shiber |
| 5,026,366 A | 6/1991 | Leckrone |
| 5,032,128 A | 7/1991 | Alonso |
| 5,037,434 A | 8/1991 | Lane |
| 5,047,041 A | 9/1991 | Samuels |
| 5,059,177 A | 10/1991 | Towne et al. |
| 5,080,668 A | 1/1992 | Bolz et al. |
| 5,085,635 A | 2/1992 | Cragg |
| 5,089,015 A | 2/1992 | Ross |
| 5,152,771 A | 10/1992 | Sabbaghian et al. |
| 5,163,953 A | 11/1992 | Vince |
| 5,167,628 A | 12/1992 | Boyles |
| 5,192,297 A | 3/1993 | Hull |
| 5,266,073 A | 11/1993 | Wall |
| 5,282,847 A | 2/1994 | Trescony et al. |
| 5,295,958 A | 3/1994 | Shturman |
| 5,332,402 A | 7/1994 | Teitelbaum |
| 5,360,444 A | 11/1994 | Kusuhara |
| 5,370,685 A | 12/1994 | Stevens |
| 5,397,351 A | 3/1995 | Pavcnik et al. |
| 5,411,055 A | 5/1995 | Kane |
| 5,411,552 A | 5/1995 | Andersen et al. |
| 5,443,446 A | 8/1995 | Shturman |
| 5,480,424 A | 1/1996 | Cox |
| 5,500,014 A | 3/1996 | Quijano et al. |
| 5,545,209 A | 8/1996 | Roberts et al. |
| 5,545,214 A | 8/1996 | Stevens |
| 5,549,665 A | 8/1996 | Vesely et al. |
| 5,554,185 A | 9/1996 | Block et al. |
| 5,558,644 A | 9/1996 | Boyd et al. |
| 5,571,175 A | 11/1996 | Vanney et al. |
| 5,584,803 A | 12/1996 | Stevens et al. |
| 5,591,185 A | 1/1997 | Kilmer et al. |
| 5,591,195 A | 1/1997 | Taheri et al. |
| 5,607,464 A | 3/1997 | Trescony et al. |
| 5,609,626 A | 3/1997 | Quijano et al. |
| 5,628,792 A | 5/1997 | Lentell |
| 5,639,274 A | 6/1997 | Fischell et al. |
| 5,665,115 A | 9/1997 | Cragg |
| 5,716,417 A | 2/1998 | Girard et al. |
| 5,728,068 A | 3/1998 | Leone et al. |
| 5,749,890 A | 5/1998 | Shaknovich |
| 5,756,476 A | 5/1998 | Epstein et al. |
| 5,769,812 A | 6/1998 | Stevens et al. |
| 5,800,508 A | 9/1998 | Goicoechea et al. |
| 5,840,081 A | 11/1998 | Andersen et al. |
| 5,855,597 A | 1/1999 | Jayaraman |
| 5,855,601 A | 1/1999 | Bessler et al. |
| 5,855,602 A | 1/1999 | Angell |
| 5,925,063 A | 7/1999 | Khosravi |
| 5,957,949 A | 9/1999 | Leonhardt et al. |
| 6,027,525 A | 2/2000 | Suh et al. |
| 6,132,473 A | 10/2000 | Williams et al. |
| 6,168,614 B1 | 1/2001 | Andersen et al. |
| 6,171,335 B1 | 1/2001 | Wheatley et al. |
| 6,174,327 B1 | 1/2001 | Mertens et al. |
| 6,210,408 B1 | 4/2001 | Chandrasekaran et al. |
| 6,217,585 B1 | 4/2001 | Houser et al. |
| 6,221,091 B1 | 4/2001 | Khosravi |
| 6,231,602 B1 | 5/2001 | Carpentier et al. |
| 6,245,102 B1 | 6/2001 | Jayaraman |
| 6,299,637 B1 | 10/2001 | Shaolian et al. |
| 6,302,906 B1 | 10/2001 | Goecoechea et al. |
| 6,350,277 B1 | 2/2002 | Kocur |
| 6,352,547 B1 | 3/2002 | Brown et al. |
| 6,425,916 B1 | 7/2002 | Garrison et al. |
| 6,440,764 B1 | 8/2002 | Focht et al. |
| 6,454,799 B1 | 9/2002 | Schreck |
| 6,458,153 B1 | 10/2002 | Bailey et al. |
| 6,461,382 B1 | 10/2002 | Cao |
| 6,468,660 B2 | 10/2002 | Ogle et al. |
| 6,482,228 B1 | 11/2002 | Norred |
| 6,488,704 B1 | 12/2002 | Connelly et al. |
| 6,527,979 B2 | 3/2003 | Constantz |
| 6,569,196 B1 | 5/2003 | Vesely |
| 6,582,462 B1 | 6/2003 | Andersen et al. |
| 6,605,112 B1 | 8/2003 | Moll et al. |
| 6,652,578 B2 | 11/2003 | Bailey et al. |
| 6,689,123 B2 | 2/2004 | Pinchasik |
| 6,716,244 B2 | 4/2004 | Klaco |
| 6,730,118 B2 | 5/2004 | Spenser et al. |
| 6,733,525 B2 | 5/2004 | Yang et al. |
| 6,767,362 B2 | 7/2004 | Schreck |
| 6,769,161 B2 | 8/2004 | Brown et al. |
| 6,783,542 B2 | 8/2004 | Eidenschink |
| 6,830,584 B1 | 12/2004 | Seguin |
| 6,878,162 B2 | 4/2005 | Bales et al. |
| 6,893,460 B2 | 5/2005 | Spenser et al. |
| 6,908,481 B2 | 6/2005 | Cribier |
| 6,936,067 B2 | 8/2005 | Buchanan |
| 7,018,406 B2 | 3/2006 | Seguin et al. |
| 7,018,408 B2 | 3/2006 | Bailey et al. |
| 7,096,554 B2 | 8/2006 | Austin et al. |
| 7,225,518 B2 | 6/2007 | Eidenschink et al. |
| 7,276,078 B2 | 10/2007 | Spenser et al. |
| 7,276,084 B2 | 10/2007 | Yang et al. |
| 7,318,278 B2 | 1/2008 | Zhang et al. |
| 7,374,571 B2 | 5/2008 | Pease et al. |
| 7,393,360 B2 | 7/2008 | Spenser et al. |
| 7,462,191 B2 | 12/2008 | Spenser et al. |
| 7,510,575 B2 | 3/2009 | Spenser et al. |
| 7,563,280 B2 | 7/2009 | Anderson et al. |
| 7,585,321 B2 | 9/2009 | Cribier |
| 7,618,446 B2 | 11/2009 | Andersen et al. |

(56)  References Cited

U.S. PATENT DOCUMENTS

| | | | |
|---|---|---|---|
| 7,618,447 B2 | 11/2009 | Case et al. | |
| 7,655,034 B2 | 2/2010 | Mitchell et al. | |
| 7,785,366 B2 | 8/2010 | Maurer et al. | |
| 7,959,672 B2 | 6/2011 | Salahieh et al. | |
| 7,993,394 B2 | 8/2011 | Hariton et al. | |
| 8,029,556 B2 | 10/2011 | Rowe | |
| 8,167,932 B2 | 5/2012 | Bourang | |
| 8,291,570 B2 | 10/2012 | Eidenschink et al. | |
| 8,449,606 B2 | 5/2013 | Eliasen et al. | |
| 8,454,685 B2 | 6/2013 | Hariton et al. | |
| 8,652,203 B2 | 2/2014 | Quadri et al. | |
| 8,747,463 B2 | 6/2014 | Fogarty et al. | |
| 9,078,781 B2 | 7/2015 | Ryan et al. | |
| 10,575,944 B2 | 3/2020 | Saar et al. | |
| 11,013,595 B2 | 5/2021 | Levi et al. | |
| 11,224,509 B2 | 1/2022 | Dasi et al. | |
| 2001/0021872 A1 | 9/2001 | Bailey et al. | |
| 2002/0026094 A1 | 2/2002 | Roth | |
| 2002/0032481 A1 | 3/2002 | Gabbay | |
| 2002/0138135 A1 | 9/2002 | Duerig et al. | |
| 2002/0173842 A1 | 11/2002 | Buchanan | |
| 2003/0050694 A1 | 3/2003 | Yang et al. | |
| 2003/0100939 A1 | 5/2003 | Yodfat et al. | |
| 2003/0158597 A1 | 8/2003 | Quiachon et al. | |
| 2003/0212454 A1 | 11/2003 | Scott et al. | |
| 2004/0039436 A1 | 2/2004 | Spenser et al. | |
| 2004/0186563 A1 | 9/2004 | Lobbi | |
| 2004/0186565 A1 | 9/2004 | Schreck | |
| 2004/0260389 A1 | 12/2004 | Case et al. | |
| 2005/0010285 A1 | 1/2005 | Lambrecht et al. | |
| 2005/0075725 A1 | 4/2005 | Rowe | |
| 2005/0075728 A1 | 4/2005 | Nguyen et al. | |
| 2005/0096736 A1 | 5/2005 | Osse et al. | |
| 2005/0188525 A1 | 9/2005 | Weber et al. | |
| 2005/0203614 A1 | 9/2005 | Forster et al. | |
| 2005/0203617 A1 | 9/2005 | Forster et al. | |
| 2005/0234546 A1 | 10/2005 | Nugent et al. | |
| 2006/0004469 A1 | 1/2006 | Sokel | |
| 2006/0025857 A1 | 2/2006 | Bergheim et al. | |
| 2006/0058872 A1 | 3/2006 | Salahieh et al. | |
| 2006/0074484 A1 | 4/2006 | Huber | |
| 2006/0149350 A1 | 7/2006 | Patel et al. | |
| 2006/0183383 A1 | 8/2006 | Asmus et al. | |
| 2006/0229719 A1 | 10/2006 | Marquez et al. | |
| 2006/0259136 A1* | 11/2006 | Nguyen | A61F 2/2412 |
| | | | 623/2.18 |
| 2006/0259137 A1 | 11/2006 | Artof et al. | |
| 2006/0287717 A1 | 12/2006 | Rowe et al. | |
| 2007/0005131 A1 | 1/2007 | Taylor | |
| 2007/0010876 A1 | 1/2007 | Salahieh et al. | |
| 2007/0010877 A1 | 1/2007 | Salahieh et al. | |
| 2007/0112422 A1 | 5/2007 | Dehdashtian | |
| 2007/0162102 A1 | 7/2007 | Ryan et al. | |
| 2007/0203503 A1 | 8/2007 | Salahieh et al. | |
| 2007/0203575 A1 | 8/2007 | Forster et al. | |
| 2007/0203576 A1 | 8/2007 | Lee et al. | |
| 2007/0213813 A1 | 9/2007 | Von Segesser et al. | |
| 2007/0233228 A1 | 10/2007 | Eberhardt et al. | |
| 2007/0260305 A1 | 11/2007 | Drews et al. | |
| 2007/0265700 A1 | 11/2007 | Eliasen et al. | |
| 2008/0114442 A1 | 5/2008 | Mitchell et al. | |
| 2008/0125853 A1 | 5/2008 | Bailey et al. | |
| 2008/0154355 A1 | 6/2008 | Benichou et al. | |
| 2008/0183271 A1 | 7/2008 | Frawley et al. | |
| 2008/0243245 A1 | 10/2008 | Thambar et al. | |
| 2008/0275537 A1 | 11/2008 | Limon | |
| 2008/0294248 A1* | 11/2008 | Yang | A61F 2/2418 |
| | | | 623/2.17 |
| 2009/0125118 A1 | 5/2009 | Gong | |
| 2009/0157175 A1 | 6/2009 | Benichou | |
| 2009/0276040 A1 | 11/2009 | Rowe et al. | |
| 2009/0281619 A1 | 11/2009 | Le et al. | |
| 2009/0299452 A1 | 12/2009 | Eidenschink et al. | |
| 2009/0319037 A1 | 12/2009 | Rowe et al. | |
| 2010/0049313 A1 | 2/2010 | Alon et al. | |

| | | | |
|---|---|---|---|
| 2010/0168844 A1 | 7/2010 | Toomes et al. | |
| 2010/0198347 A1 | 8/2010 | Zakay et al. | |
| 2010/0204781 A1 | 8/2010 | Alkhatib | |
| 2011/0015729 A1 | 1/2011 | Jimenez et al. | |
| 2011/0066224 A1 | 3/2011 | White | |
| 2011/0137397 A1 | 6/2011 | Chau et al. | |
| 2011/0218619 A1 | 9/2011 | Benichou et al. | |
| 2011/0230956 A1* | 9/2011 | White | A61F 2/844 |
| | | | 623/1.24 |
| 2011/0238168 A1* | 9/2011 | Pellegrini | A61F 2/2433 |
| | | | 623/2.17 |
| 2011/0319991 A1 | 12/2011 | Hariton et al. | |
| 2012/0089223 A1 | 4/2012 | Nguyen et al. | |
| 2012/0101571 A1 | 4/2012 | Thambar et al. | |
| 2012/0123529 A1 | 5/2012 | Levi et al. | |
| 2012/0259409 A1 | 10/2012 | Nguyen et al. | |
| 2012/0316642 A1* | 12/2012 | Yu | A61F 2/2412 |
| | | | 623/2.38 |
| 2013/0023985 A1 | 1/2013 | Khairkhahan et al. | |
| 2013/0046373 A1 | 2/2013 | Cartledge et al. | |
| 2013/0150956 A1 | 6/2013 | Yohanan et al. | |
| 2013/0166017 A1 | 6/2013 | Cartledge et al. | |
| 2013/0190857 A1 | 7/2013 | Mitra et al. | |
| 2013/0274873 A1 | 10/2013 | Delaloye et al. | |
| 2013/0310926 A1 | 11/2013 | Hariton | |
| 2013/0317598 A1 | 11/2013 | Rowe et al. | |
| 2013/0331929 A1 | 12/2013 | Mitra et al. | |
| 2014/0005771 A1* | 1/2014 | Braido | A61F 2/2412 |
| | | | 623/2.12 |
| 2014/0194981 A1 | 7/2014 | Menk et al. | |
| 2014/0200661 A1 | 7/2014 | Pintor et al. | |
| 2014/0209238 A1 | 7/2014 | Bonyuet et al. | |
| 2014/0222136 A1 | 8/2014 | Geist et al. | |
| 2014/0277417 A1 | 9/2014 | Schraut et al. | |
| 2014/0277419 A1 | 9/2014 | Garde et al. | |
| 2014/0277424 A1 | 9/2014 | Oslund | |
| 2014/0277563 A1 | 9/2014 | White | |
| 2014/0330372 A1 | 11/2014 | Weston et al. | |
| 2014/0343671 A1 | 11/2014 | Yohanan et al. | |
| 2014/0350667 A1 | 11/2014 | Braido et al. | |
| 2015/0073545 A1 | 3/2015 | Braido | |
| 2015/0073546 A1 | 3/2015 | Braido | |
| 2018/0200054 A1* | 7/2018 | Spenser | A61F 2/9524 |
| 2018/0344456 A1 | 12/2018 | Barash et al. | |

FOREIGN PATENT DOCUMENTS

| | | |
|---|---|---|
| DE | 2246526 A1 | 3/1973 |
| DE | 19532846 A1 | 3/1997 |
| DE | 19546692 A1 | 6/1997 |
| DE | 19857887 A1 | 7/2000 |
| DE | 19907646 A1 | 8/2000 |
| DE | 10049812 A1 | 4/2002 |
| DE | 10049813 C1 | 4/2002 |
| DE | 10049814 A1 | 4/2002 |
| DE | 10049815 A1 | 4/2002 |
| EP | 0103546 A1 | 3/1984 |
| EP | 0850607 A1 | 7/1998 |
| EP | 1057460 A1 | 12/2000 |
| EP | 1088529 A2 | 4/2001 |
| EP | 1570809 A1 | 9/2005 |
| FR | 2788217 A1 | 7/2000 |
| FR | 2815844 A1 | 5/2002 |
| GB | 2056023 A | 3/1981 |
| SU | 1271508 A1 | 11/1986 |
| WO | 9117720 A1 | 11/1991 |
| WO | 9217118 A1 | 10/1992 |
| WO | 9301768 A1 | 2/1993 |
| WO | 9724080 A1 | 7/1997 |
| WO | 9829057 A1 | 7/1998 |
| WO | 9930646 A1 | 6/1999 |
| WO | 9933414 A1 | 7/1999 |
| WO | 9940964 A1 | 8/1999 |
| WO | 9947075 A1 | 9/1999 |
| WO | 0018333 A1 | 4/2000 |
| WO | 0041652 A1 | 7/2000 |
| WO | 0047139 A1 | 8/2000 |
| WO | 0135878 A2 | 5/2001 |

(56) References Cited

FOREIGN PATENT DOCUMENTS

| WO | 0149213 | A2 | 7/2001 |
|---|---|---|---|
| WO | 0154624 | A1 | 8/2001 |
| WO | 0154625 | A1 | 8/2001 |
| WO | 0162189 | A1 | 8/2001 |
| WO | 0164137 | A1 | 9/2001 |
| WO | 0176510 | A2 | 10/2001 |
| WO | 0222054 | A1 | 3/2002 |
| WO | 0236048 | A1 | 5/2002 |
| WO | 0241789 | A2 | 5/2002 |
| WO | 0243620 | A1 | 6/2002 |
| WO | 0247575 | A2 | 6/2002 |
| WO | 0249540 | A2 | 6/2002 |
| WO | 03047468 | A1 | 6/2003 |
| WO | 2005034812 | A1 | 4/2005 |
| WO | 2005055883 | A1 | 6/2005 |
| WO | 2005084595 | A1 | 9/2005 |
| WO | 2005102015 | A2 | 11/2005 |
| WO | 2006014233 | A2 | 2/2006 |
| WO | 2006032051 | A2 | 3/2006 |
| WO | 2006034008 | A2 | 3/2006 |
| WO | 2006111391 | A1 | 10/2006 |
| WO | 2006127089 | A1 | 11/2006 |
| WO | 2006138173 | A2 | 12/2006 |
| WO | 2007047488 | A2 | 4/2007 |
| WO | 2007067942 | A1 | 6/2007 |
| WO | 2007097983 | A2 | 8/2007 |
| WO | 2008005405 | A2 | 1/2008 |
| WO | 2008015257 | A2 | 2/2008 |
| WO | 2008035337 | A2 | 3/2008 |
| WO | 2008091515 | A2 | 7/2008 |
| WO | 2008147964 | A1 | 12/2008 |
| WO | 2008150529 | A1 | 12/2008 |
| WO | 2009033469 | A1 | 3/2009 |
| WO | 2009042196 | A2 | 4/2009 |
| WO | 2009053497 | A1 | 4/2009 |
| WO | 2009061389 | A2 | 5/2009 |
| WO | 2009094188 | A2 | 7/2009 |
| WO | 2009116041 | A2 | 9/2009 |
| WO | 2009149462 | A2 | 12/2009 |
| WO | 2010011699 | A2 | 1/2010 |
| WO | 2010121076 | A2 | 10/2010 |
| WO | 2013106585 | A1 | 7/2013 |
| WO | 2015085218 | A1 | 6/2015 |
| WO | 2019154124 | A1 | 8/2019 |

OTHER PUBLICATIONS

H.R. Andersen "History of Percutaneous Aortic Valve Prosthesis," Herz No. 34. pp. 343-346. 2009.

Pavcnik, et al. "Development and initial Experimental Evaluation of a Prosthetic Aortic Valve for Transcatheter Placement," Cardiovascular Radiology, vol. 183, No. 1. pp. 151-154. 1992.

Bailey, S. "Percutaneous Expandable Prosthetic Valves," Textbook of Interventional Cardiology vol. 2, 2nd Ed. pp. 1268-1276. 1994.

Al-Khaja, et al. "Eleven Years' Experience with Carpentier-Edwards Biological Valves in Relation to Survival and Complications," European Journal of Cardiothoracic Surgery, vol. 3. pp. 305-311. 1989.

Ross, "Aortic Valve Surgery," At a meeting of the Council on Aug. 4, 1966. pp. 192-197.

Sabbah, et al. "Mechanical Factors in the Degeneration of Porcine Bioprosthetic Valves: An Overview," Journal of Cardiac Surgery, vol. 4, No. 4. pp. 302-309. 1989.

Wheatley, "Valve Prostheses," Operative Surgery, 4th ed. pp. 415-424. 1986.

Uchida, "Modifications of Gianturco Expandable Wire Stents," American Journal of Roentgenology, vol. 150. pp. 1185-1187. 1986.

Walther T, Dehdashtian MM, Khanna R, Young E, Goldbrunner PJ, Lee W. Trans-catheter valve-in-valve implantation: in vitro hydrodynamic performance of the SAPIEN+cloth trans-catheter heart valve in the Carpentier-Edwards Perimount valves. Eur J Cardiothorac Surg. 2011;40(5): 1120-6. Epub Apr. 7, 2011.

* cited by examiner

Lc3

Lc4

PROSTHETIC HEART VALVES

CROSS-REFERENCE TO RELATED APPLICATIONS

This application is a continuation of International Patent Application No. PCT/US2020/045577 filed Aug. 10, 2020, which claims the benefit of U.S. Provisional Patent Application No. 62/885,556 filed Aug. 12, 2019, which are both incorporated by reference herein.

FIELD

This disclosure is related to prosthetic heart valves having a radially collapsible and expandable mechanical frame and scalloped valve leaflets attached to struts of the frame.

BACKGROUND

Some assembly methods of leaflets to a prosthetic valve include attaching the leaflets via a series of suture loops to frame struts their scallop suture lines. Since the leaflets are also attached to the frame via commissures at their opposing lateral ends, changes in frame diameter, such as transitions from a fully expanded state to a compressed state during a crimping procedure, in which the longitudinal distance between opposing junctions of frame cells increases, can result in stretching and compression of the leaflets and high stress concentrations along suture loops. Moreover, systole and diastole cycles acting on the frame when the prosthetic valve is implanted may result in abrasion of the suture loops and the leaflets at the attachment regions.

SUMMARY

Disclosed herein are several novel techniques for construction of prosthetic heart valves, particularly techniques for attachment of scalloped edges of valvular leaflets to struts of mechanical frames using sutures and/or other materials as intermediate coupling members.

Some exemplary prosthetic heart valves comprise a radially expandable and collapsible annular frame comprising a plurality of intersecting struts coupled together at mechanical pivot joints, wherein radial expansion or contraction of the annular frame causes the intersecting struts to pivot relative to one another at the pivot joints, and a valvular structure mounted within the frame that regulates blood flow through the prosthetic heart valve, the valvular structure comprising leaflets; wherein the leaflets are coupled to the frame at lateral commissure ends of the leaflets and along scalloped edges of the leaflets that extend between the commissure ends; and wherein the scalloped edges of the leaflets are coupled to the segments of the struts of the frame via suture loops, and the strut segments to which the suture loops are coupled are oriented substantially perpendicular to the scalloped edges of the leaflets.

The coupling of the scalloped edges of the leaflets to strut segments that are oriented substantially perpendicular to the scalloped edges allows movement of the scalloped edges relative to the strut segments via the suture loops sliding along the strut segments during radial expansion and compression of the frame. During systole and diastole, anatomical forces acting on the leaflets at attachment points to the struts along the scalloped edges can be substantially perpendicular to the suture loops, thereby inhibiting undesirable abrasion of the suture loops and the leaflets.

In some embodiments, the scalloped edge of each leaflet is coupled via suture loops to segments of at least six different struts of the frame. For example, the at least six different struts can comprise three parallel strut segments on one side of the scalloped edge and another three parallel strut segments on a second side of the scalloped edge.

Some exemplary prosthetic heart valves comprise a scallop line infrastructure that comprises three scallop line elements, with each of the three scallop line elements being attached to a scalloped edge of a respective one of the three leaflets; wherein each of the scallop line elements comprises two opposing end portions and a central portion between the two opposing end portions, wherein the end portions are attached to the frame along with lateral ends of the leaflets at commissures, and wherein the central portions are attached to the scalloped edges of the leaflets and are free of the frame. In some such embodiments, the scallop line elements are formed of a rigid material, such as metal or metal alloy, and are resiliently deformable to resist radially inward displacement of the scalloped edges of the leaflets. In other embodiments, the scallop line elements are formed of a soft material, such as a short skirt, cloth, cable, or string. In some embodiments, the scallop line elements are flexible to allow the central portions of the scallop line elements to deform from a generally U shape to a generally V shape during radial compression of the frame while the end portions of the scallop line elements move toward each other.

In some exemplary prosthetic heart valves, each leaflet scalloped edge is coupled to strut segments via a cloth strip, wherein a first end of the cloth strip is attached to the scalloped edge and a second opposite end of the cloth strip is separately attached to the strut segments. In some such embodiments, the first end of the cloth strip is attached to the scalloped edge via first sutures, and the second end of the cloth strip is attached to the strut segments via second sutures discrete from the first sutures. In some embodiments, the second sutures are looped around the strut segments and portions of the first end of the cloth strip. In some embodiments, the first end of the cloth strip extends around at least two sides of the strut segments.

In some prosthetic heart valves, the struts of the frame comprise plural strut segments between the pivot joints, and at least some of the strut segments are tapered in width between the pivot joints. In some such embodiments, the strut segments are tapered such that the reduce in width moving from the inflow end toward the outflow end. In some embodiments, leaflets are coupled to the tapered strut segments via suture loops that extend around the tapered strut segments, such that the suture loops are large enough to fit around narrower ends of the tapered strut segments and small enough to not fit around wider ends of the tapered strut segments. The suture loops can be configured to slide along the tapered strut segments from the narrowed ends toward the wider ends and become frictionally stuck or 'self-locked' at an intermediate location along the tapered strut segments where the suture loops are equal in circumference to the strut segments.

In some prosthetic heart valves, each scalloped edge is attached to adjacent segments of intersecting struts via sliding suture loops, the adjacent segments joining at a common pivot joint of the pivot joints, wherein the sliding suture loops are permitted to slide along the adjacent segments both toward and away from the common pivot joint. During radial frame expansion, the sliding suture loops can slide along the adjacent segments toward the common pivot joint, and during radial frame compression, the sliding suture loops can slide along the adjacent segments away from the common pivot joint.

The foregoing and other objects, features, and advantages of the disclosed technology will become more apparent from the following detailed description, which proceeds with reference to the accompanying figures.

DETAILED DESCRIPTION

Disclosed herein are novel prosthetic heart valves and related components, systems, and methods. Some disclosed embodiments include new ways of attaching each leaflet to struts of a radially expandable and radially collapsible frame, where discrete struts of the frame are pivotably coupled to one another at strut junctions (e.g., a mechanical frame). The new ways of attaching the leaflets to the struts can include embodiments where the scalloped portions of the leaflets are sutured to adjacent struts that are transverse or substantially perpendicular to the scallop stitch line, instead of to struts that are substantially parallel thereto. In some embodiments, suture loops by which the leaflets are attached to the struts can be slidably movable along the respective struts, configured to enable displacement of the scallop edge of the leaflets along the longitudinal/axial direction, thereby reducing stress concentrations acting on the suture loops and on the leaflets at the attachment regions of the suture loops.

Figure 1:
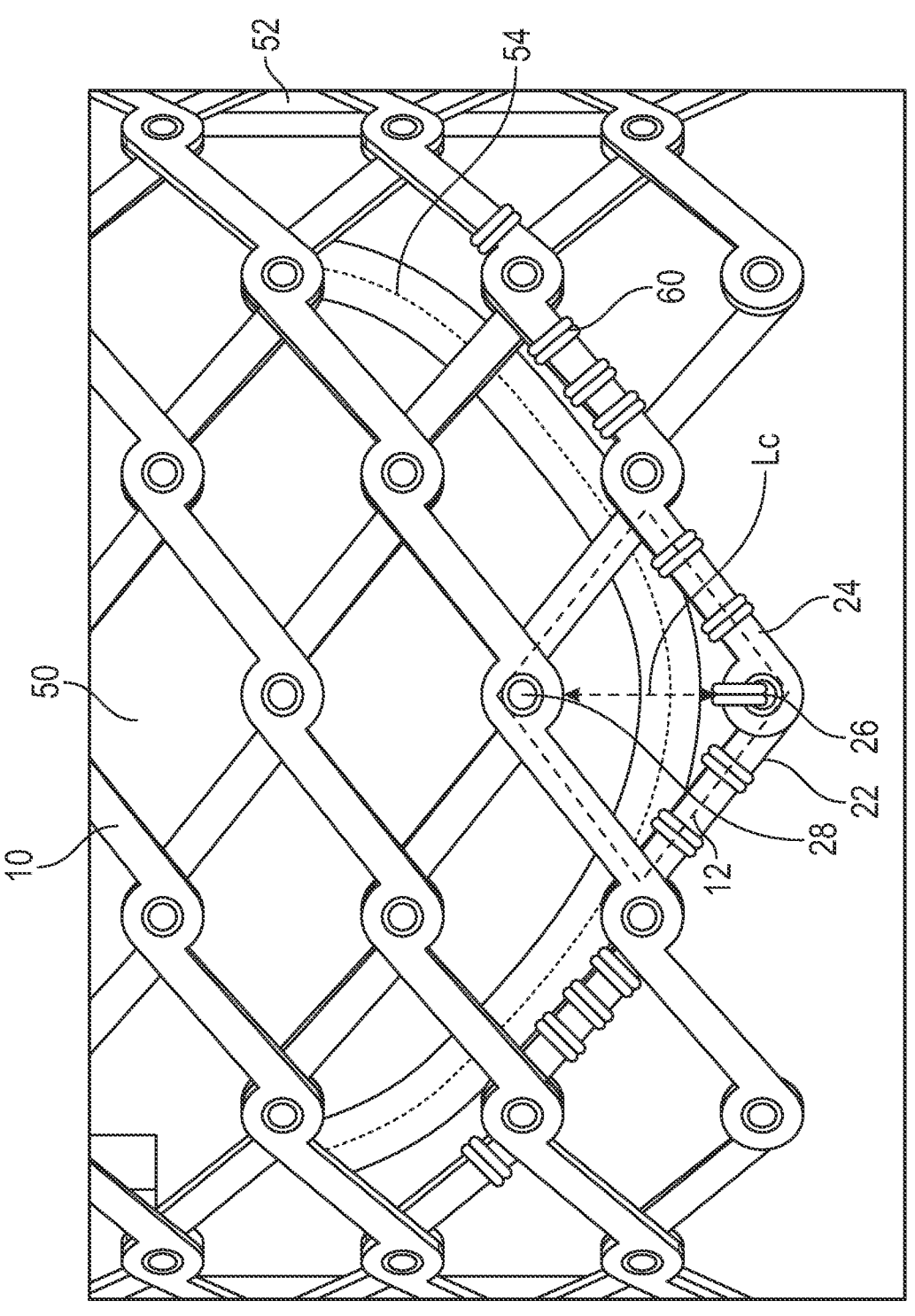
FIG. 1 shows a portion of a prosthetic heart valve, illustrating coupling of a leaflet to the frame.

FIG. 1 shows an example of an attachment of a leaflet 50 to a frame 10 of a prosthetic valve. The frame 10 can comprise a plurality of overlapping struts joined at strut junctions, which can comprise mechanical pivot joints. The struts can comprise a first group of struts that are generally parallel to one another and extend diagonally in a first direction (or chirality), which can include the strut 22 for example, and the struts can comprise a second group of struts that are generally parallel to one another and extend diagonally in a second direction (or chirality) that is transverse to the first direction, which can include the strut 24 for example. The struts of the first group of struts can be joined via pivot joints to the struts of the second group of struts where they overlap/intersect (e.g., strut junctions 26 and 28). Either group of struts can overly the other group of struts, as shown in FIG. 1. The struts pivot at the strut junctions when the frame 10 radially expands and radially collapses. When the frame is fully expanded, the struts are oriented more circumferentially, and when the frame is radially collapsed, the struts are oriented more axially.

A prosthetic valve can include a plurality of leaflets 50, for example three leaflets, each being attached to the frame 10 via two opposing commissures 52 (shown at the sides of FIG. 1) and along its scalloped edge. A scallop stitch line 54 is shown in FIG. 1, for example used to attach an inner skirt to the scalloped region of the leaflet 50. The leaflet 50 extends past the scallop stich line 54 and is further attached via suture loops 60 to struts of the valve frame that are generally parallel to the scallop stitch line 54. In this example, the leaflet 50 is attached via suture loops 60 to struts 22 and 24, generally parallel to scallop stitch line 54. The suture loops 60 are placed along the struts 22 and 24 down to an intersection point at strut junction 26.

The frame 10 is shown in FIG. 1 in an expanded state, wherein an exemplary cell 12 is demarcated with dashed lines. The frame cell 12 has a longitudinal distance Lc between two opposing strut junctions 26 and 28. When the frame 10 is radially compressed, for example during a crimping process, the distance Lc between junctions 26 and 28 is elongated, in some cases up to twice its distance in a fully expanded state, thereby stretching the leaflet 50 in the axial direction, which can result in high stress concentration along suture loops 60.

Another disadvantage of the configuration of FIG. 1 is that when an implanted prosthetic valve is subjected to pulsating systole and diastole cycles, the oscillating motion of the frame 10 applies further stress concentrations in the suture loops 60.

In other embodiments, the valve is constructed using method of stitching each leaflet along its scalloped edge to struts which are perpendicular to the scallop stitch line via slidable suture loops, instead of struts which are parallel to the scallop stitch line as in FIG. 1.

Figure 2A:
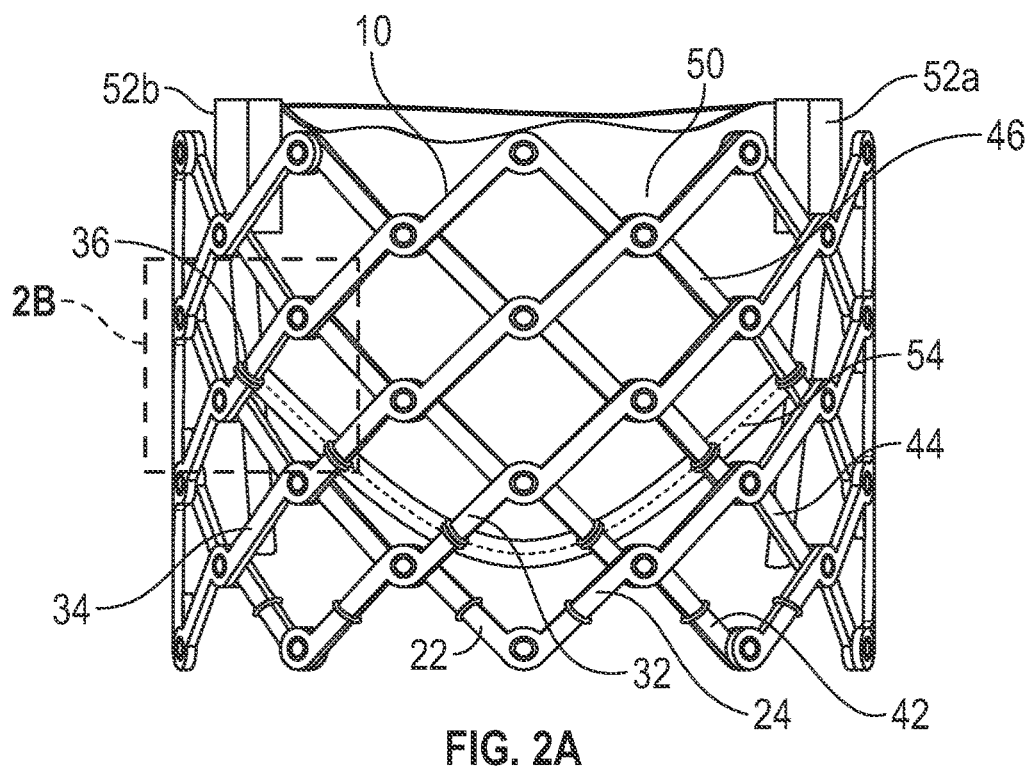
FIG. 2A shows another prosthetic heart valve, illustrating coupling of a leaflet to the frame.
Figure 2B:
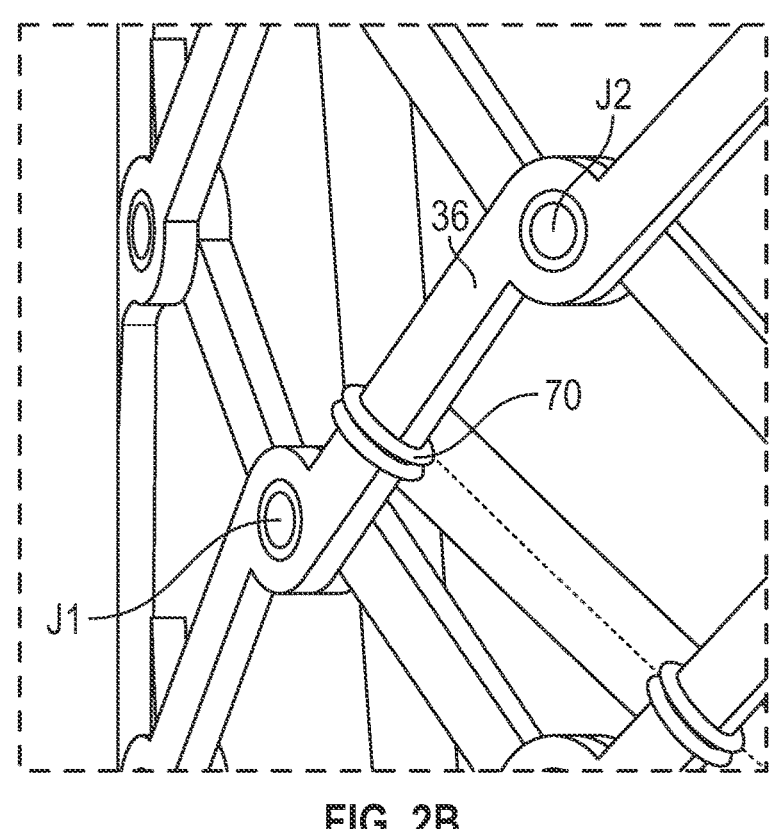
FIG. 2B is an enlarged view of a portion of FIG. 2A.

FIGS. 2A and 2B show a prosthetic valve embodiment where a leaflet 50 is attached to a fully expanded frame 10 at two commissures 52a, 52b and at struts 32, 34, 36, 42, 44 and 46, all transverse and/or substantially perpendicular to the scallop stitch line 54, via suture loops 70, and not to struts 22 or 24.

FIG. 2B shows a zoomed in view of region 2B of FIG. 2A. A suture loop 70 is shown in FIG. 2B attaching the scalloped edge of the leaflet 50 to the strut 36 between the junctions J1 and J2 thereof. The suture 70, positioned in FIG. 2B adjacent to junction J1, can slide between these two adjacent junctions, relieving stress build up.

Figure 3A:
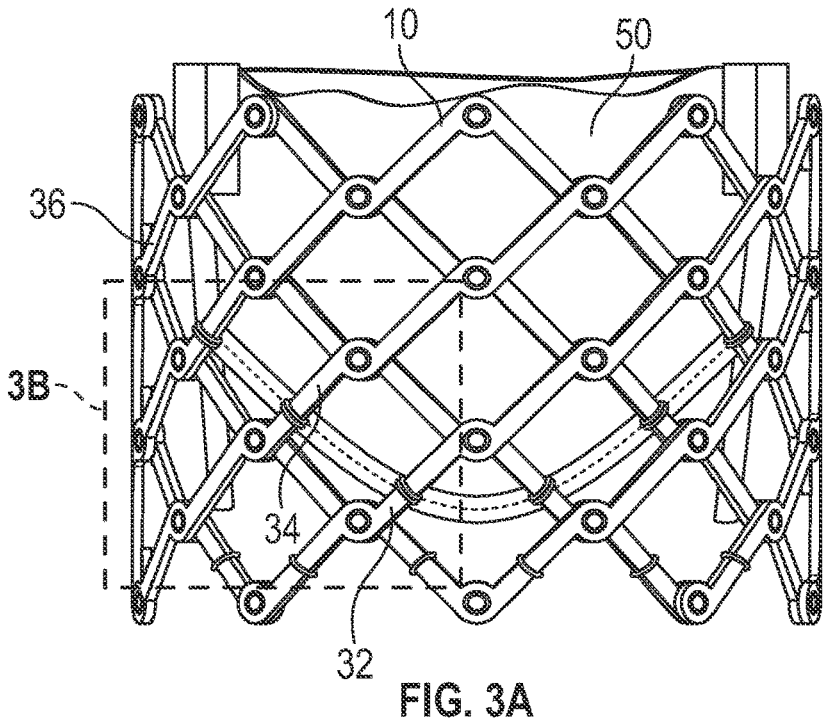
FIG. 3A shows another prosthetic heart valve, illustrating coupling of a leaflet to the frame.
Figure 3B:
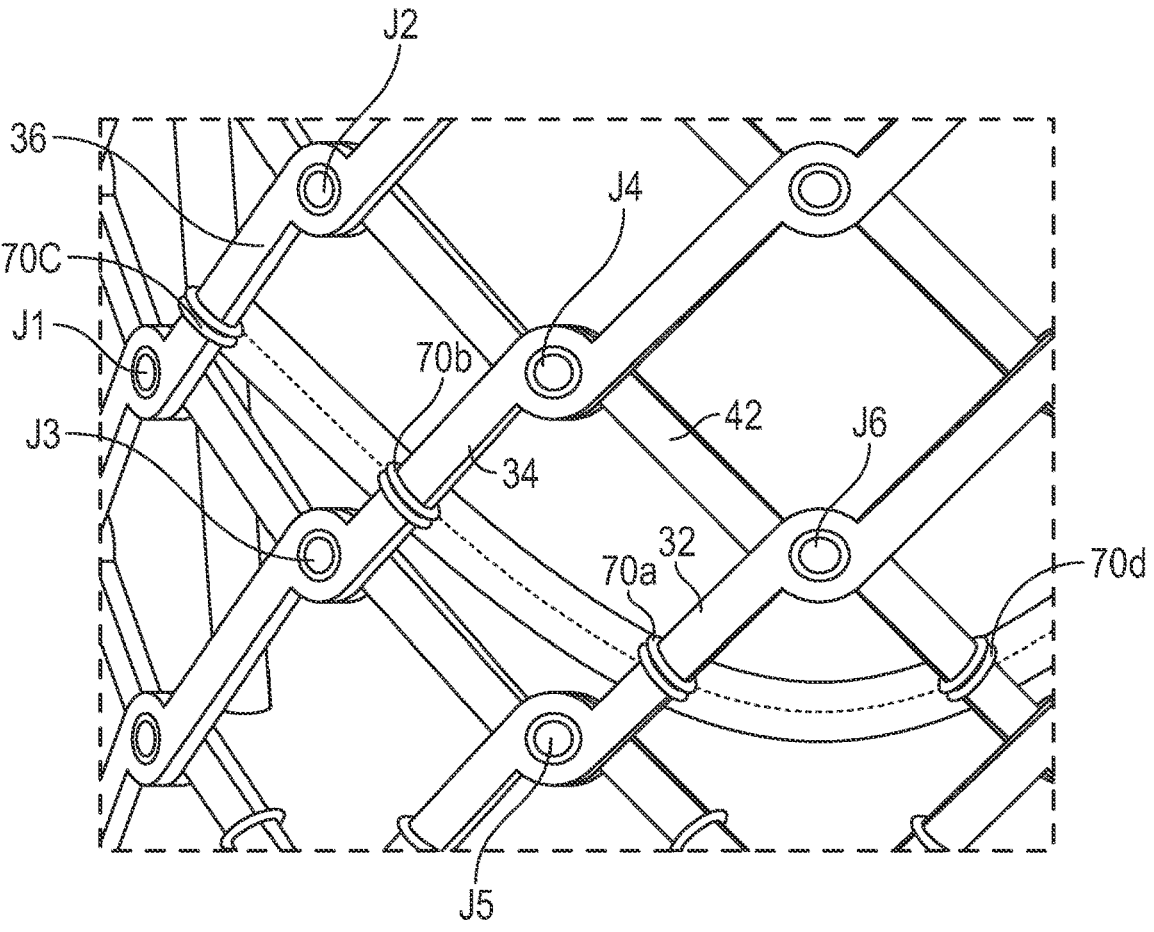
FIG. 3B is an enlarged view of a portion of FIG. 2A.

FIG. 3A shows a leaflet 50 attached to the frame 10 as in FIG. 2A, wherein the frame 10 in FIG. 3A is slightly compressed relative to its state in FIG. 2A. FIG. 3B shows a zoomed in view of region 3B of FIG. 3A. Suture loops 70a, 70b and 70c attach the leaflet 50 to struts 32, 34 and 36, respectively. As shown in FIG. 3B, each suture loop 70 can slide along a respective strut, responding to forces acting there upon as a result of the state and geometry of the frame 10, as well as the structural configuration and attachment regions of the scalloped edge of the leaflet 50. Suture loop 70a is slidably movable between junctions J5 and J6. Suture loop 70b is slidably movable between junctions J3 and J4. Suture loop 70c is slidably movable between junctions J1 and J2. While suture loop 70c is positioned closer to one of the junctions, namely J1, suture loops 70b and 70a are positioned closer to the mid-portions between their corresponding junctions.

Figure 4A:
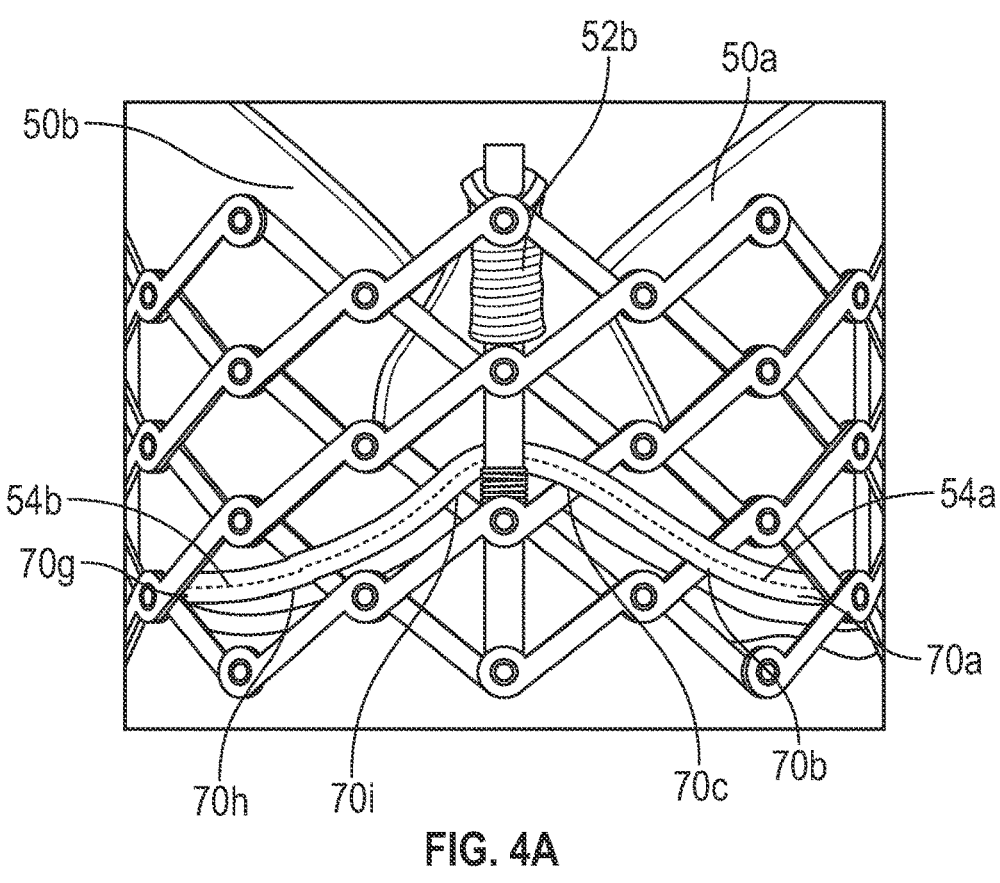
FIGS. 4A and 4B illustrates another prosthetic heart valve, illustrating coupling of leaflets to the frame.
Figure 4B:
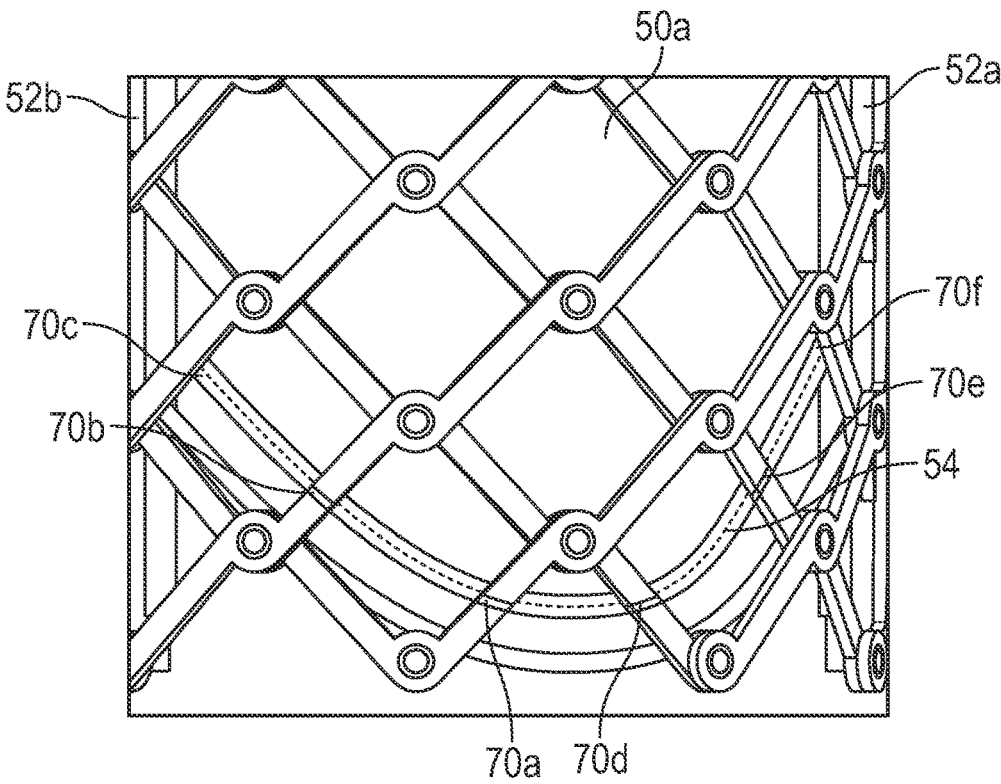

FIG. 4A shows two adjacent leaflets 50a and 50b attached to the frame 10. Both leaflets 50a and 50b are attached to a supporting strut of the frame via commissure 52b. The leaflet 50a is shown attached to struts substantially perpendicular to scallop stitch line 54 via suture loops 70a, 70b and 70c. The leaflet 50b is shown attached to struts substantially perpendicular to scallop stitch line 54 via suture loops 70g, 70h and 70i. FIG. 4B shows the leaflet 50a, attached to the frame at two commissures 52a and 52b, and attached to struts substantially perpendicular to scallop stitch line 54 via suture loops 70a, 70b, 70c, 70d, 70e and 70f.

Figures 5A, 5B:
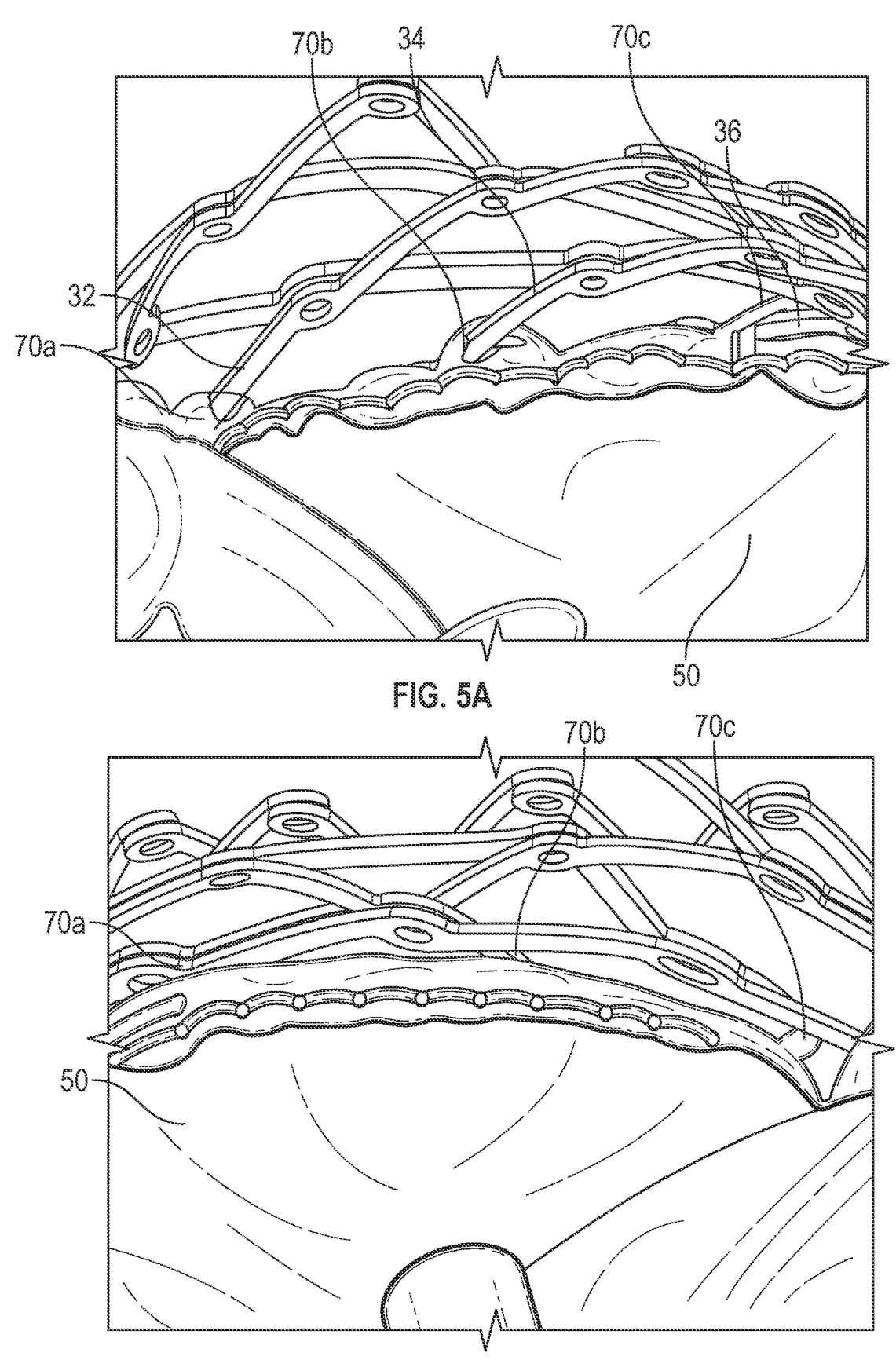
FIGS. 5A and 5B are internal views of a prosthetic heart valve, illustrating coupling of leaflets to the frame.

FIGS. 5A and 5B show a top view of the leaflet 50 attached to struts substantially perpendicular to scallop stitch line 54, such as struts 32, 34 and 34, via suture loops 70a, 70b and 70c, respectively.

Figure 6A:
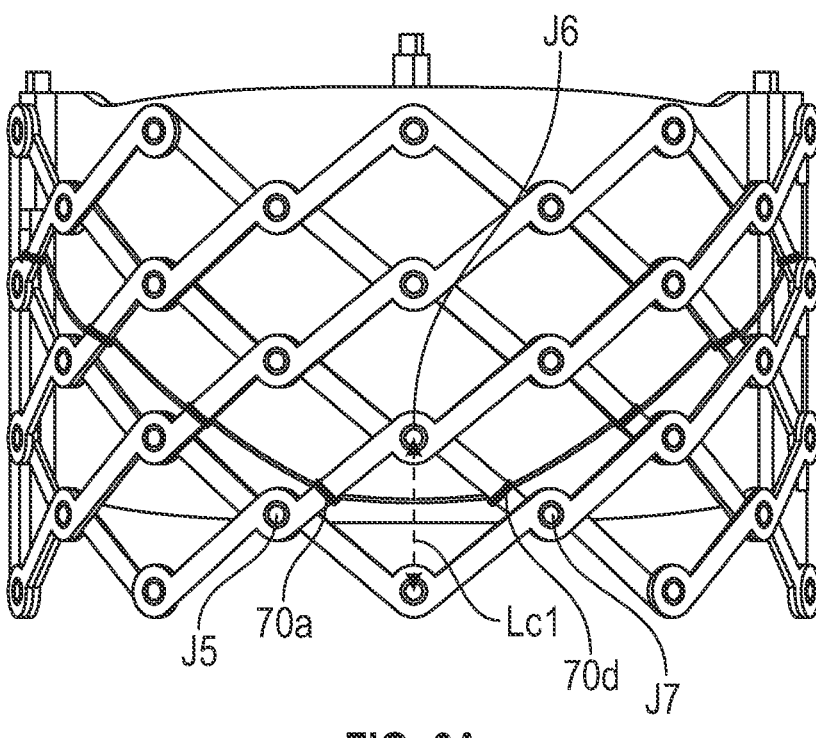
FIGS. 6A-6E show various stages of radial compression of a prosthetic heart valve, illustrating changes in dimensions of frame cells.
Figure 6B:
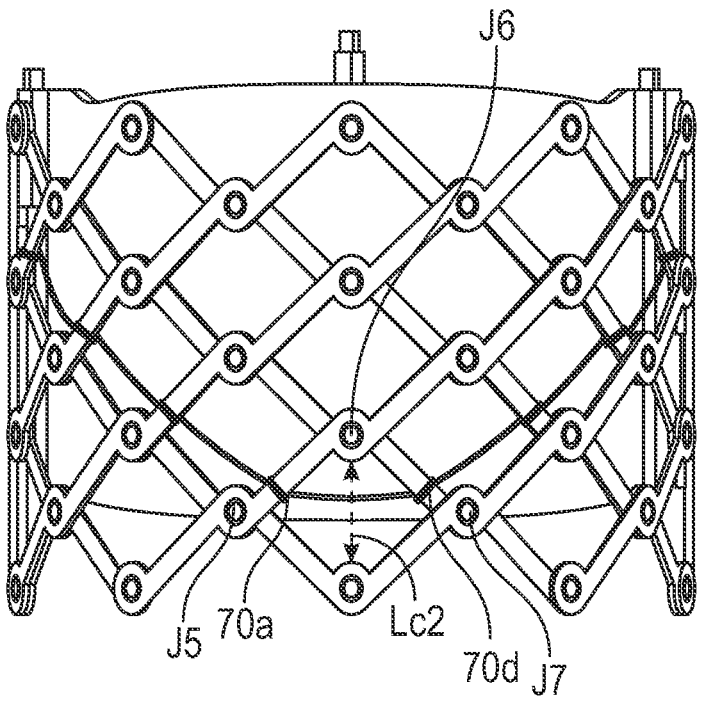
Figure 6C:
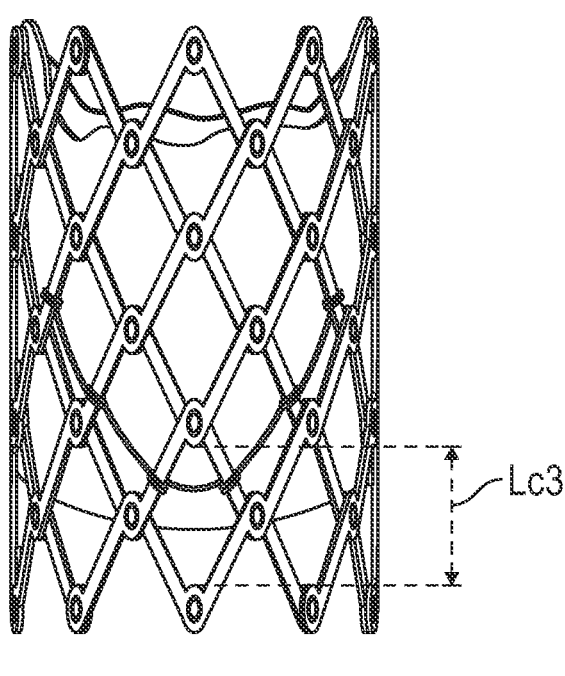
Figure 6D:
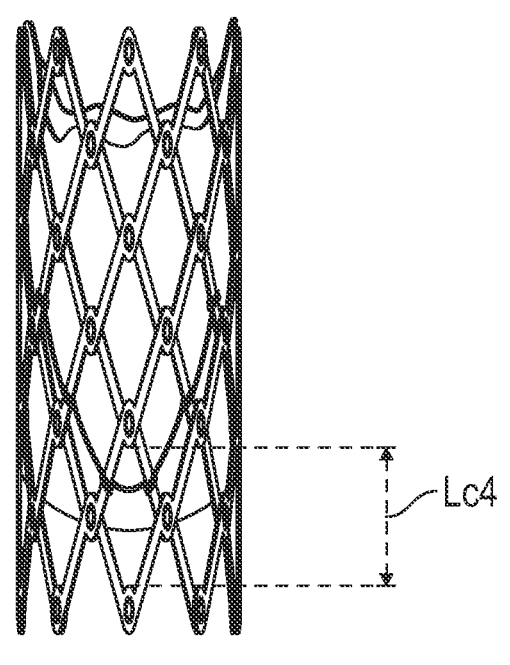
Figure 6E:
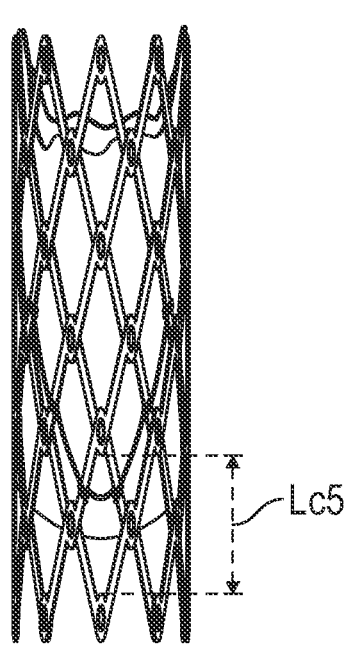

FIGS. 6A-6E show different transition stages between a radially expanded frame (FIG. 6A) and a radially compressed frame (FIG. 6E). The longitudinal distance Lc between two opposing junctions of a cell of the frame is increasing from Lc1 to LcS, such that Lc1<Lc2<Lc3<Lc4<Lc5. Suture loop 70a is slidably movable between junction J5 and J6, and suture loop 70b is slidably movable between junctions J7 and J6. The position of the suture loops 70a and 70b changes along the struts between their respective junctions according to the changing frame diameter.

Advantageously, this disclosed configuration of leaflet attachment to the frame allows movement of the scalloped edge along the struts during expansion or compression of the frame, while avoiding the stress concentrations developed in the vicinity of suture loops 60 due to stretching of the leaflet according to the prior art mode of attachment exemplified in FIG. 1.

A further advantage is that during systole and diastole, the forces acting on the leaflet at its attachment points to the struts is normal to the suture loops 70 attachments, thereby inhibiting undesirable abrasion of the suture loops and the leaflets.

Figure 7:
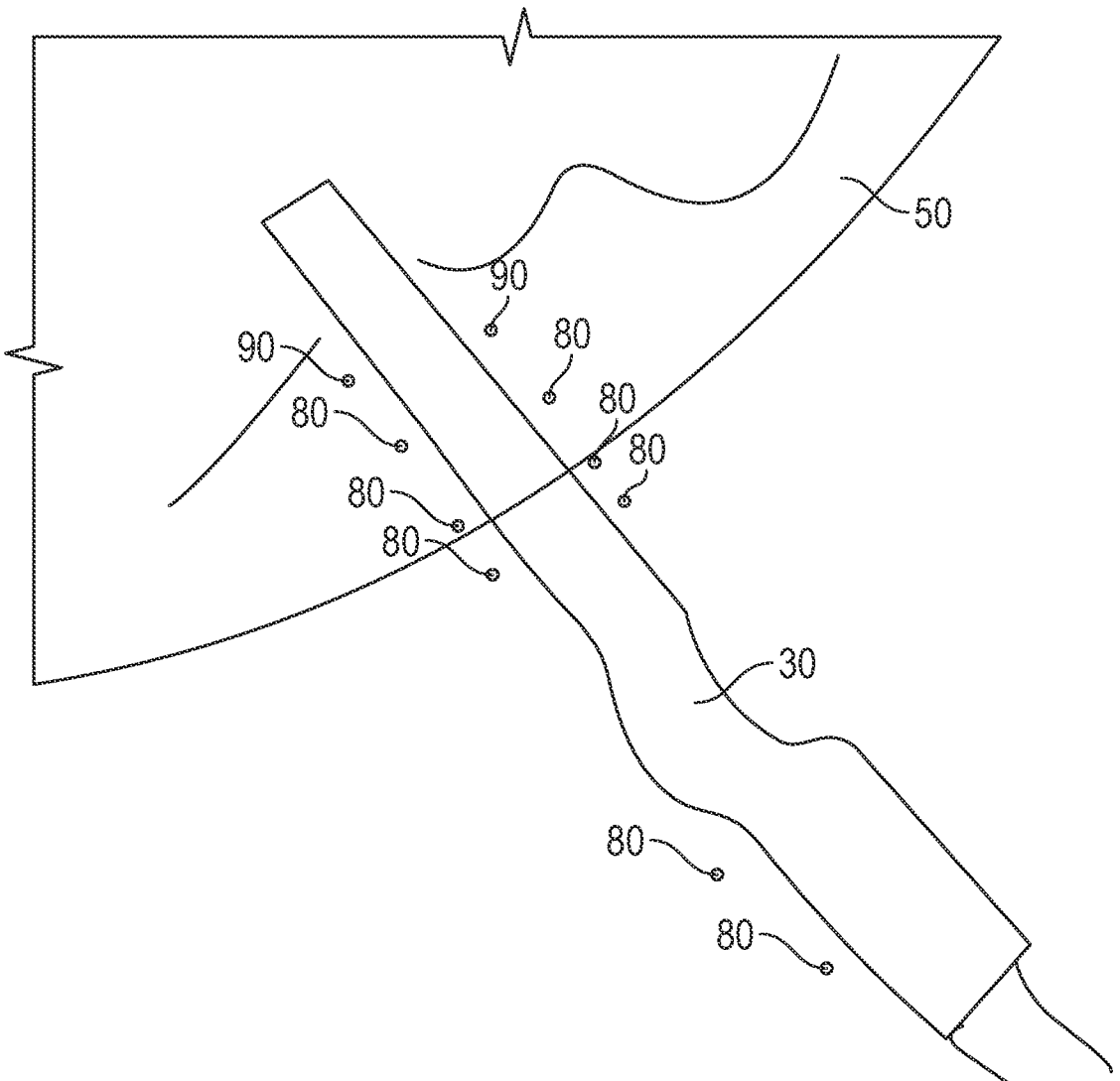
FIG. 7 shows an exemplary suturing scheme for coupling a leaflet to a frame strut.

According to some embodiments, the struts are provided with apertures along their lengths, and the leaflets are provided apertures along the circumference of their scallop line, the apertures being adapted to receive suture loops 70 there through. FIG. 7 shows a strut 30 provided with a plurality of aperture couples 80 at different positions along its length, and a portion of a leaflet 50 provided with one couple of apertures 90, such that the leaflet can be positioned over the struts, aligning its apertures 90 with a matching couple of strut apertures. Advantageously, this configuration can facilitate attachment of the leaflets 50 to the struts 30. According to some embodiments, the suture loops 70 are not attached too tightly to the struts, but rather are loose enough so as to enable them to slide along the respective struts.

A further advantage of the current configuration is that it allows leaflet design optimization, without being restricted to a designs in which leaflets need to be continuously attached to struts substantially parallel to the scallop stitch line.

Some prosthetic valves can be constructed by attaching the leaflets to a skirt attached to their scallop line, wherein the skirt is sutured to struts substantially parallel to their scallop suture lines. In some embodiments, the skirt is sutured both to struts substantially parallel to the scallop suture line and to struts substantially perpendicular. Since the leaflets are also attached to the frame via commissures at their opposing longitudinal ends, changes in frame diameter, such as transitions from a fully expanded state to a compressed state during a crimping procedure, in which the longitudinal distance between opposing junctions of frame cells increases, can result in stretching the leaflets and high stress concentrations developed therein.

In some embodiments, a prosthetic valve can include a scallop line infrastructure that comprises three scallop line elements, with each line element configured to be attached to a respective leaflet. Each scallop line element can include two opposing end portions, and a central portion disposed between the end portions. The central portion can be attached (for example, sutured) to the cusp edge of a leaflet. The end portions can be connected to the frame (along with the leaflets) at the commissures. The central portion can be free of the frame (i.e. not attached to any struts of the frame). The scallop line element can be formed of a flexible material, allowing it to compress from a U-shape to a V-shape during frame compression/crimping. The scallop line element can also be formed of a rigid material (such as metal, Nitinol, etc.), and can be spring biased against the frame. The scallop line element can also be formed of a soft material (short skirt, cloth, cable, string etc.), which can be connected by at least one suture loop to at least one strut, in order to prevent inward radial displacement of the central portion. In some embodiments, the scallop line element is configured to prevent formation of folds within the leaflet at any diameter of frame.

Figure 7A:
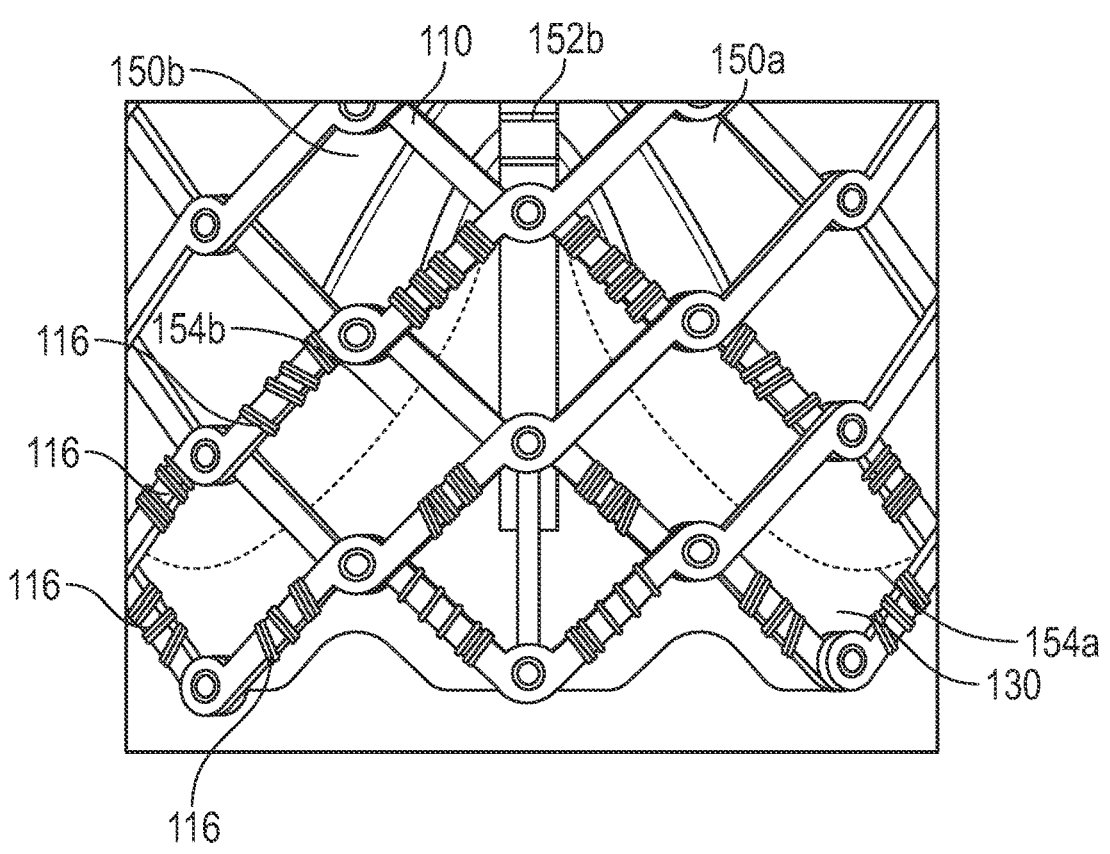
FIGS. 7A and 7B show a portion of a prosthetic heart valve, illustrating coupling of leaflets to the frame.
Figure 7B:
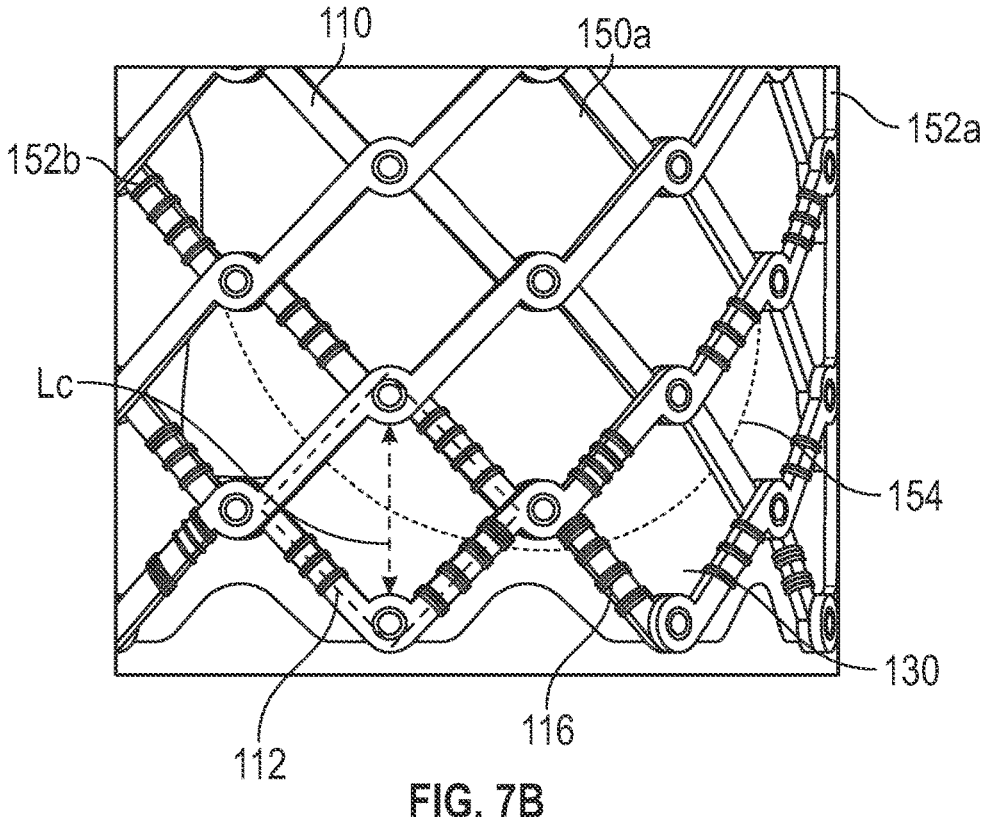

FIGS. 7A-7B show an example of conventional attachment of leaflets to a frame of a prosthetic valve. FIG. 7A shows two adjacent leaflets 150a and 150b attached to the frame 110. Both leaflets 150*a* and 150*b* are attached to a supporting strut of the frame via commissure 152*b*. Leaflets 150*a* and 150*b* are sutured to an inner skirt 130 via scallop stitch lines 154*a* and 154*b*. FIG. 7B shows the leaflet 150*a* attached to the frame at two commissures 152*a* and 152*b*. Leaflets 150*a* is sutured to inner skirt 130 via scallop stitch line 154. The skirt 130 is shown attached to struts both substantially perpendicular and substantially parallel to scallop stitch lines 154*a*, 154*b* via suture loops 116.

The frame 110 is shown in FIG. 7B in an expanded state, wherein an exemplary cell 112 is shown with a longitudinal distance Lc between two opposing junctions. When the frame 110 is radially compressed, for example during a crimping process, the distance Lc is elongated, in some cases up to twice its distance in a fully expanded state. The stretching of the skirt 130 is transferred to a corresponding displacement of the leaflet 150*a* due to its connection with the skirt 130 at scallop suture line 154, thereby stretching the leaflet 150*a* in the axial direction as well, which results in high stress concentration along suture loops 116 as well as scallop suture line 154.

Another disadvantage of this configuration is that when an implanted prosthetic valve is subjected to pulsating systole and diastole cycles, the oscillating motion of the frame 110 applies further stress concentrations in the suture loops 116 and the scallop suture line 154.

Figure 8A:
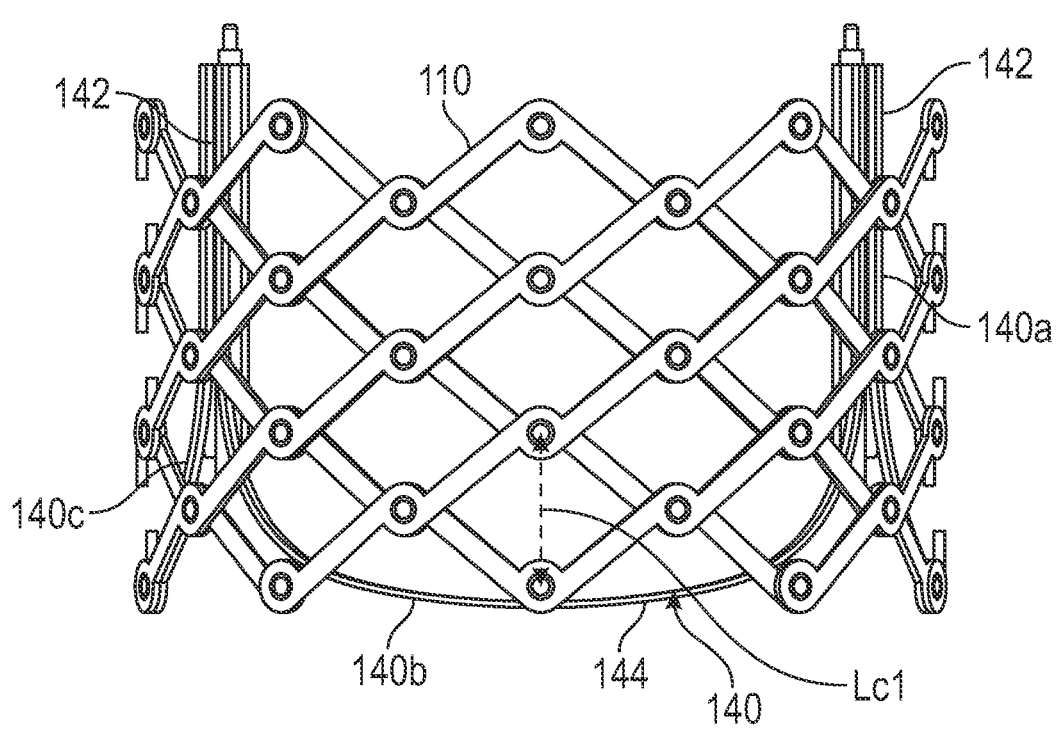
FIGS. 8A-8C show various stages of radial compression of a prosthetic heart valve, illustrating changes in dimensions of frame cells.
Figure 8B:
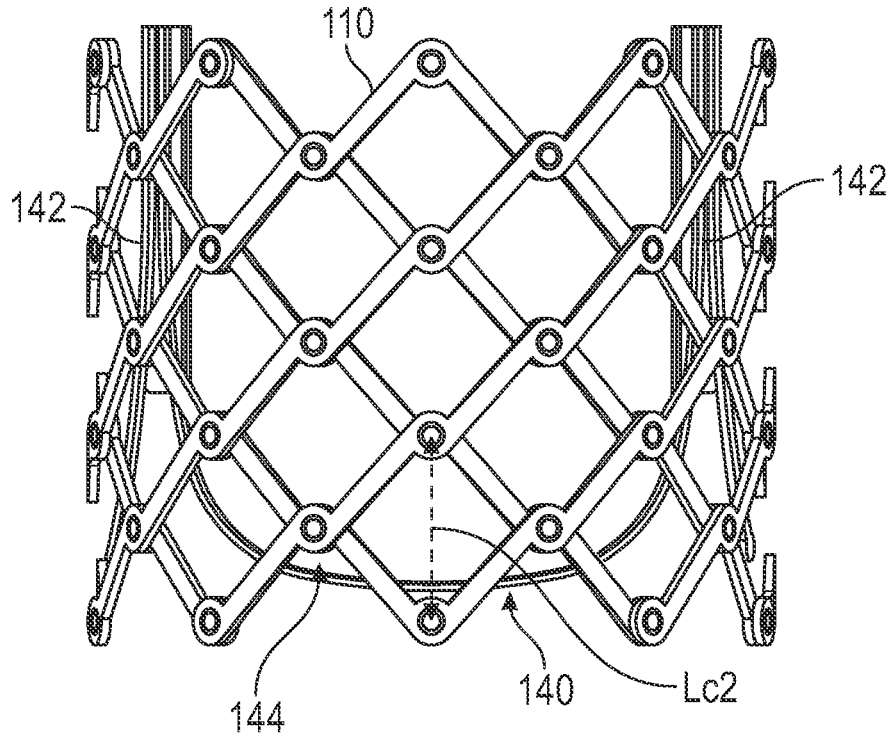
Figure 8C:
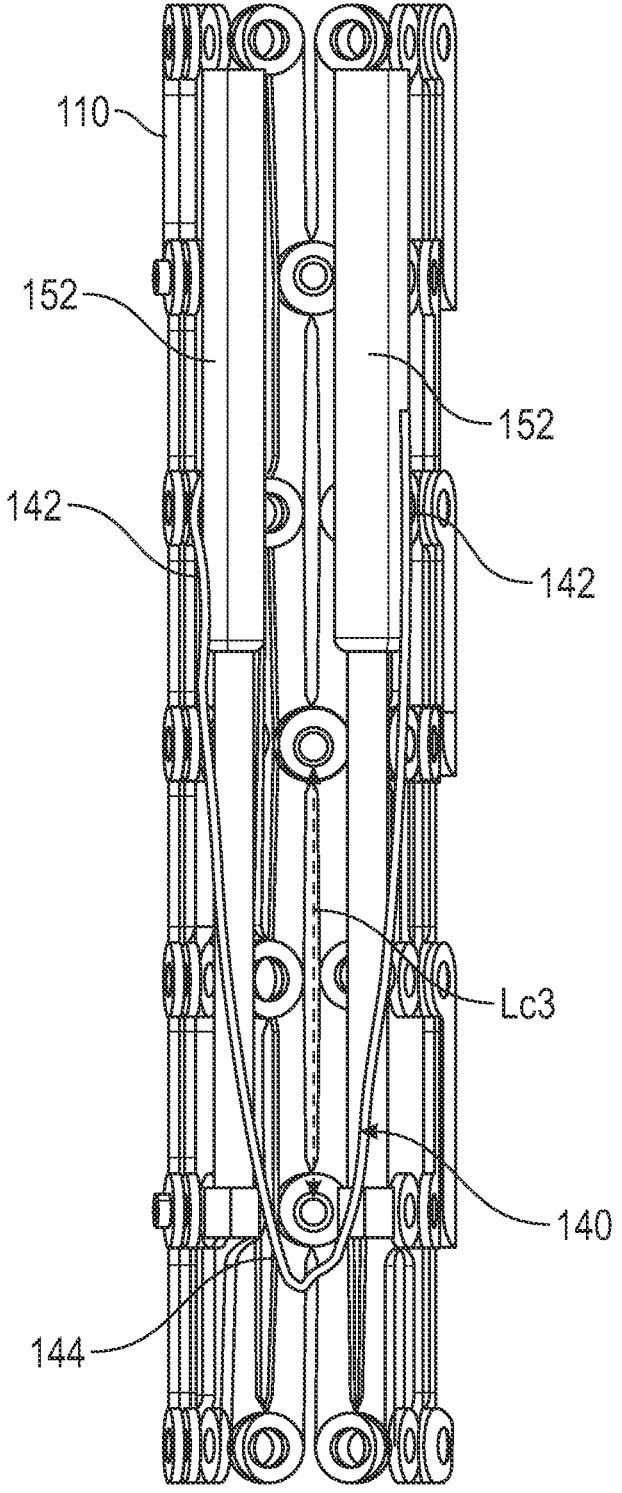

With reference to FIGS. 8A-8C, some exemplary prosthetics valves employ a method of stitching each leaflet along its cusp edge to a scallop line element 140, wherein the scallop line element is attached to the frame at least at the commissures. A prosthetic valve can include a plurality of leaflets, for example three leaflets, each being attached to the frame 110 via two opposing commissures and along its scalloped edge. FIG. 8A shows three scallop line elements 140*a*, 140*b* and 140*c*, configured to attach via sutures (for example) to the cusp edges of leaflets 150*a*, 150*b* and 150*c*, respectively (not shown in FIGS. 8A-8C for simplicity). Each scallop line element comprises two opposing end portions 142, configured to extend towards the commissure attachment regions of a leaflet 150, and a central portion 144 disposed between the end portion 142, configured to follow the geometry of the cusp edge. The scallop line elements 140*a*, 140*b* and 140*c* may be formed as separate elements. According to some embodiments, the scallop line elements 140*a*, 140*b*, 140*c* can be attached to each other (for example, at end portions 142), together forming a scallop line infrastructure 140. According to some embodiments, the scallop line elements 140*a*, 140*b*, 140*c* are pre-assembled to form the scallop line infrastructure 140, such that all of the cusp edges of all leaflets can be attached (e.g. sutured) to the scallop line infrastructure 140. According to some embodiments, all scallop line elements are integrally formed as a single scallop line infrastructure 140. FIGS. 8A-8C show different transition stages between a radially expanded frame (FIG. 8A) and a compressed frame (FIG. 8C). The longitudinal distance Lc between two opposing junctions of a cell of the frame is increasing from Lc1 to Lc2, such that Lc1<Lc2<Lc3.

According to some embodiments, only the end portions 142 are attached to the frame 110, together with the leaflet 150, at the commissures 152, while the central portion 144, attached to the cusp edge of the leaflet, is not attached to any frame struts, being loosely disposed around the inner surface of the frame 110.

The scallop line element 140 is provided with internal flexibility, configured to enable its central portion 144 to compress while the opposing end portions 142 are moving towards each other during frame compression (see FIG. 8C).

Preferably, the scallop line element 140 is designed to keep an optimized leaflet shape during valve performance as well as during transitions between frame states, to prolong its durability. Specifically, the scallop line element 140 is designed to prevent formation of folds within the leaflet 150 at any diameter of frame 140. According to some embodiments, the scallop line element 140 is made from a relatively rigid material, configured to prevent any deformations thereof aside from the desired flexibility of the central portion 144 during diameter change of the frame 110. According to some embodiments, scallop line element 140 is formed of a wire (e.g. a laser cut wire), such as Cobalt Chrome or Nitinol. According to some embodiments, the scallop line element 140 is spring-biased against the inner surface of the frame 110, so as to prevent inward radial displacement of the central portion 144.

According to some embodiments, scallop line element 140 is made of a soft material, such as a string, a cable, a suture, a cloth and the like. According to some embodiments, the scallop line element 140 further comprises at least one attachment point (e.g. via a suture loop) of the central portion 144 to at least one strut, so as to prevent inward radial displacement of the central portion 144.

Advantageously, most of the axial forces will transfer via the arcuate structure of the disclosed geometry of the scallop line element 140 towards the attachment regions of the end portions 142 to the commissures 152.

Figure 9A:
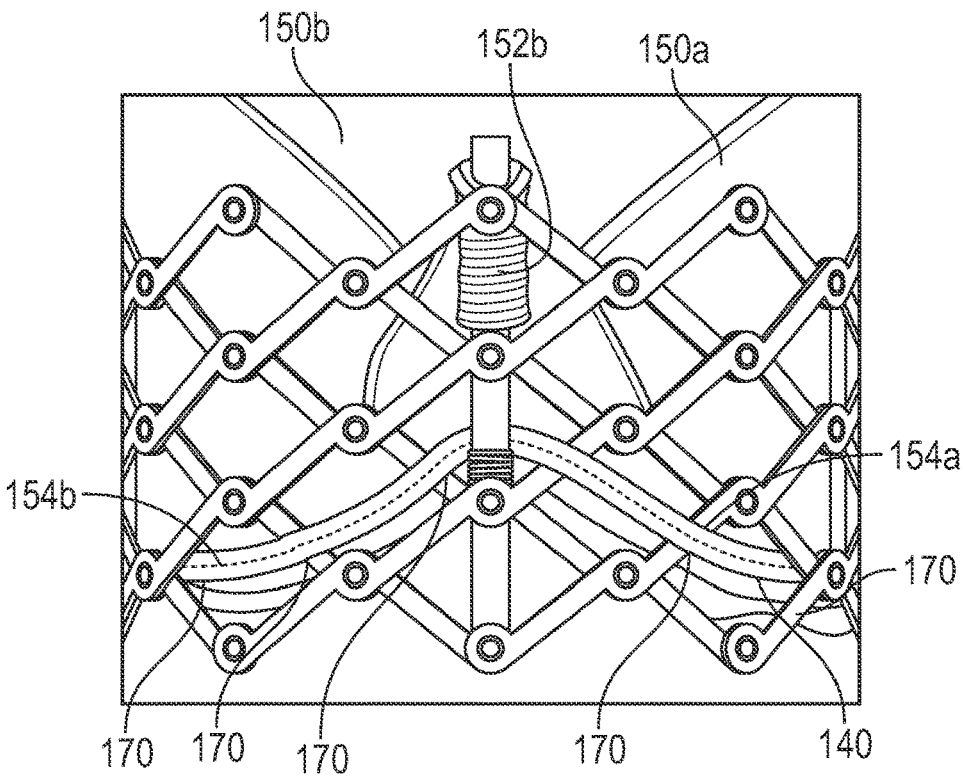
FIGS. 9A and 9B show a portion of a prosthetic heart valve, illustrating coupling of leaflets to the frame.

Some embodiments comprise leaflets attached to a scallop line infrastructure using a short skirt or a cloth strip. FIG. 9A shows two adjacent leaflets 150*a* and 150*b* attached to supporting struts of the frame via commissure 152*b*. The leaflets 150*a* and 150*b* are attached to the scallop line infrastructure 140 via scallop suture lines 154*a* and 154*b*, respectively. FIG. 9A shows the leaflet 150*a* attached to the frame at two commissures 152*a* and 152*b*. Where the scallop line infrastructure 140 in the embodiment depicted in FIGS. 9A-9B is made of a flexible material such as cloth, it can be attached to struts of the frame 110 via several suture loops 170, so as to prevent inward radial displacement of the central portion 144.

Figure 9B:
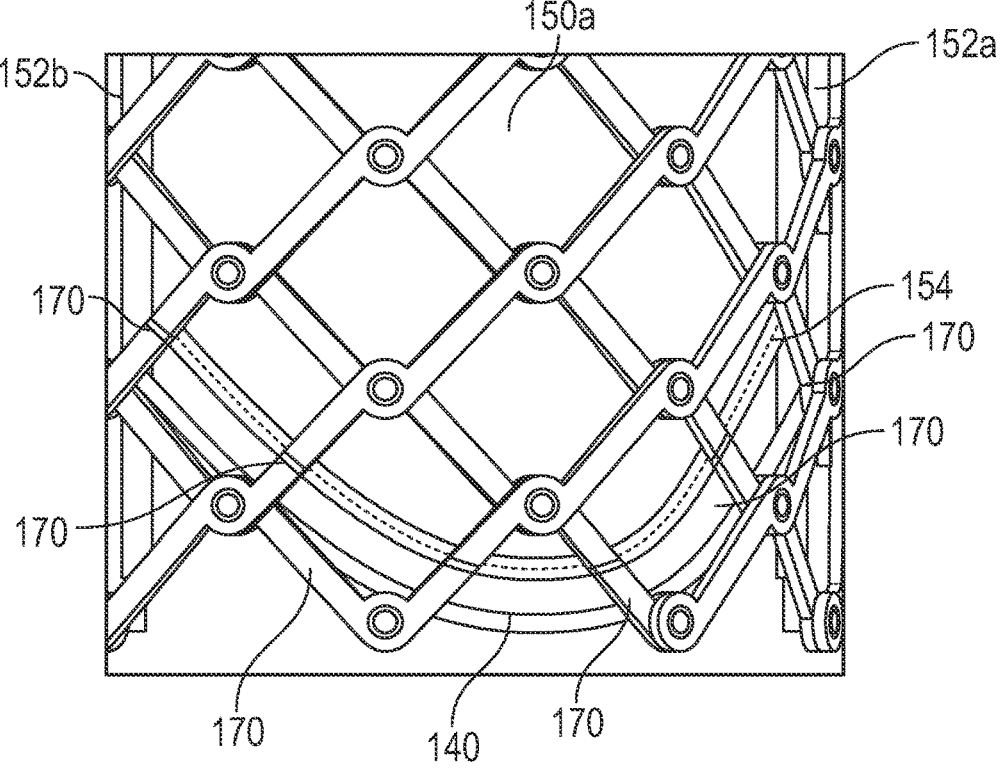

In the embodiments shown in FIGS. 9A-9B, the mode of attachment to the frame 110 can be such that the scallop line infrastructure 140 is attached via suture loops 170 to struts which are substantially perpendicular to the scallop stitch line 154, wherein each suture loop 170 can slide along its respective strut.

According to some embodiments, the scallop line infrastructure 140 comprises a cloth strip surrounding a reinforcing member, such as a reinforcement strip, disposed between the cloth and the cusp edge of the leaflet sutured thereto.

Figure 10A:
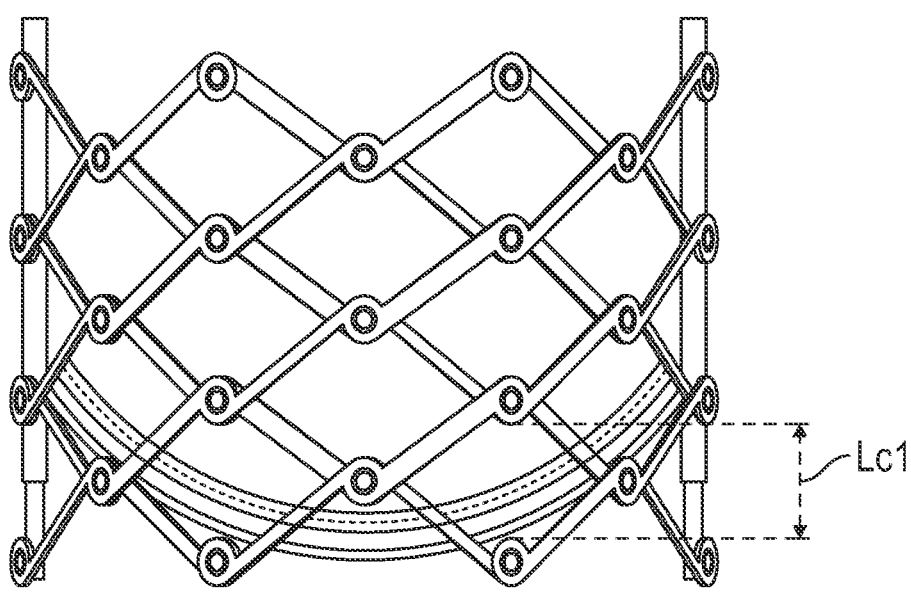
FIGS. 10A-10F show various stages of radial compression of a prosthetic heart valve, illustrating changes in dimensions of frame cells.
Figure 10B:
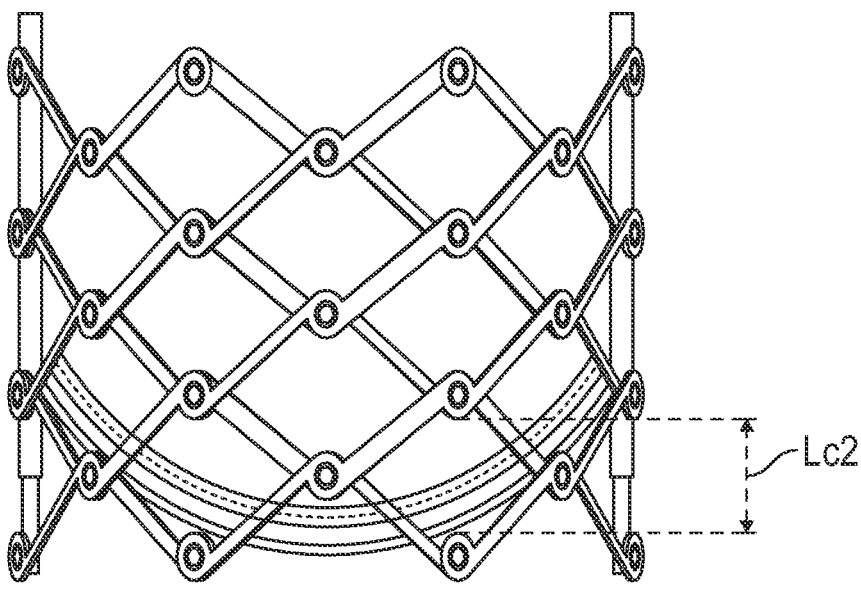
Figures 10C, 10D:
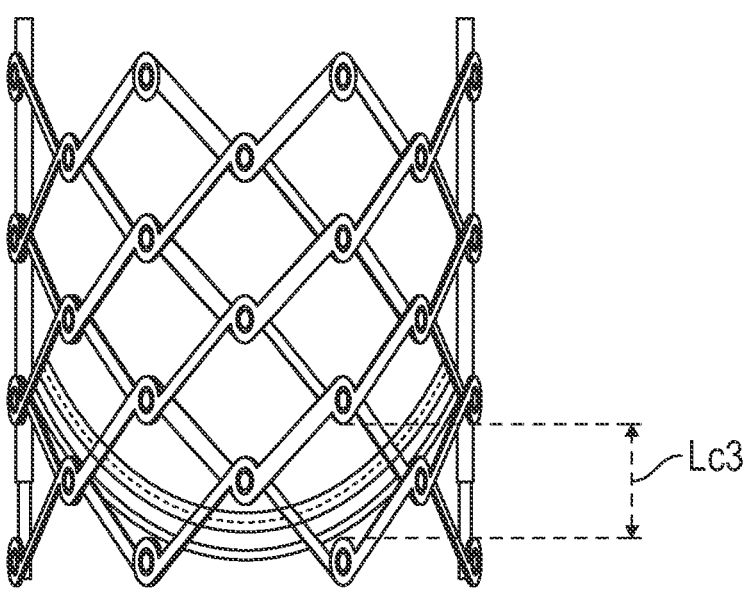
Figure 10E:
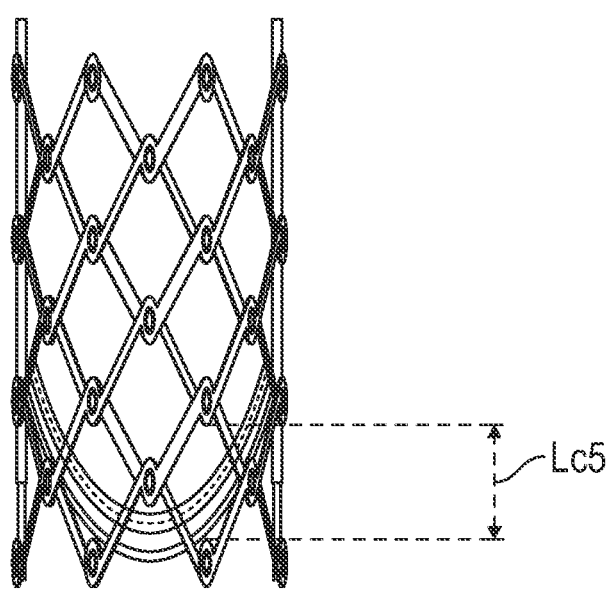
Figure 10F:
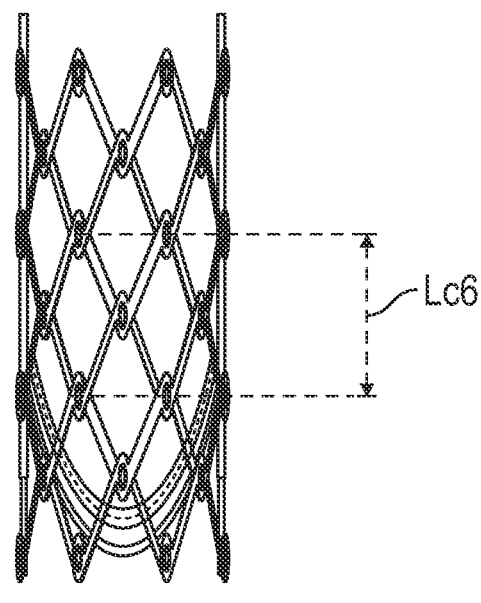

FIGS. 10A-10F show different transition stages between a radially expanded frame (FIG. 10A) and a radially compressed frame (FIG. 10F). The longitudinal distance Lc between two opposing junctions of a cell of the frame is increasing from Lc1 to Lc6, such that Lc1<Lc2<Lc3<Lc4<Lc5>Lc6. The position of the suture loops 170 changes along the struts between their respective junctions according to the changing frame diameter.

While the configuration of the embodiments shown in FIGS. 9A-10F may present a disadvantage of approximating suture loops 170 of adjacent struts towards each other in the crimped configuration (e.g., FIG. 10F), the embodiment depicted in FIGS. 8A-8C avoid such risks as the scallop line infrastructure 140 is not connected to the struts via any such suture loops.

Some assembly methods of attaching leaflets to a frame in prosthetic valves include attaching the leaflets to cloth strips (forming a skirt) via a scallop stitch line, and attaching the leaflets together with the cloth strips to frame struts via a series of suture loops. This process can pose several challenges, however. Such challenges can include (1) difficulties arising from stitching the suture loops through the cloth strips and the leaflet tissue (compared to a potential much easier process, if the loops can be stitched through a cloth strip without a leaflet); (2) difficulties in attaching the leaflet to the strut in close proximity to the scallop line, which requires expertise to provide high accuracy and repeatability of the process; (3) the cloth of the skirt may suffer from high abrasion, resulting in low long-term durability; and (4) attaching the skirt to numerous struts requires long assembly times.

To overcome these issues, leaflets can be attached to the frame by first suturing a cloth strip (inner skirt) to the leaflet via a scallop stitch line and then attaching the cloth strip to the struts by suture loops extending through the cloth and around the struts. This results in the leaflet being indirectly attached to the strut via the cloth strip, i.e. without being directly sutured to the strut itself. The attachment process is thus significantly simplified, and assembly time is shortened. The cloth can be provided with pre-cut stitch holes for the scallop stitch line and the suture loops. The holes can follow the geometrical pattern of the struts, such as a zig-zag pattern, thereby improving assembly tie and accuracy. The cloth strip can also act as a soft hinge connection. The distance between the scallop stitch line and the suture loops can be more precisely controlled.

Figure 11:
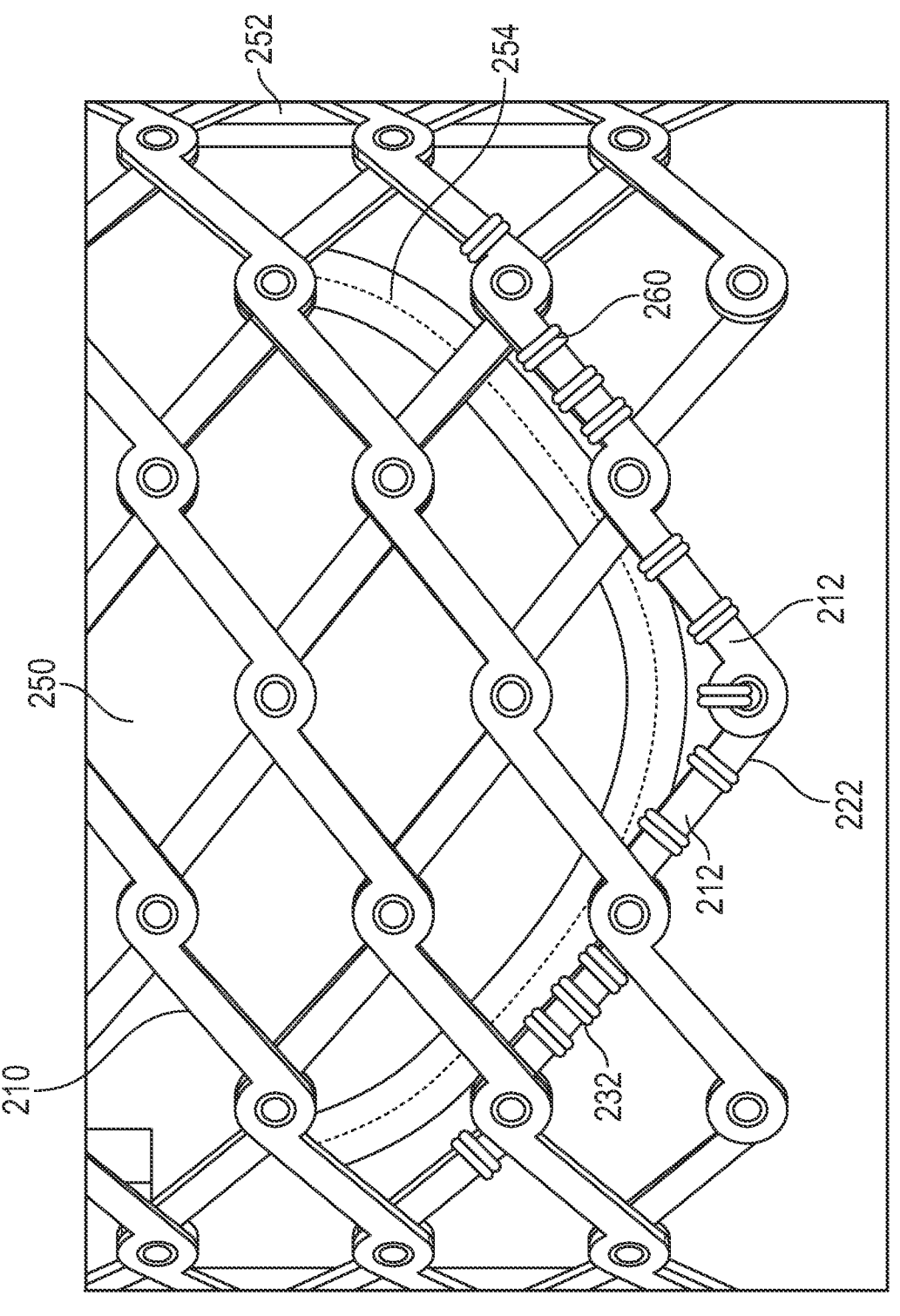
FIG. 11 shows a portion of a prosthetic heart valve, illustrating coupling of a leaflet to the frame.

FIG. 11 shows one type of attachment of a leaflet 250 to a frame 210 of a prosthetic valve. A prosthetic valve can include a plurality of leaflets 250 each attached to the frame 210 via two opposing commissures 252 and along its scalloped edge. A scallop stitch line 254 is shown in FIG. 11, used to attach a skirt to the scalloped region of the leaflet 250. According to some embodiments, the skirt can include a first cloth 232, positioned between the scallop line of a leaflet 250 and a strut 212, and a second cloth 234 (see FIG. 13) attached to the opposite surface of the scallop line of the leaflet 250, facing the internal lumen of the frame 210.

As shown in FIG. 11, a leaflet is attached via suture loops 260 to the struts 212, wherein the suture loops 260 extend through the first and second cloths 232, 234, through the cusp edge of the leaflet 250, and around the struts 212.

Figure 12A:
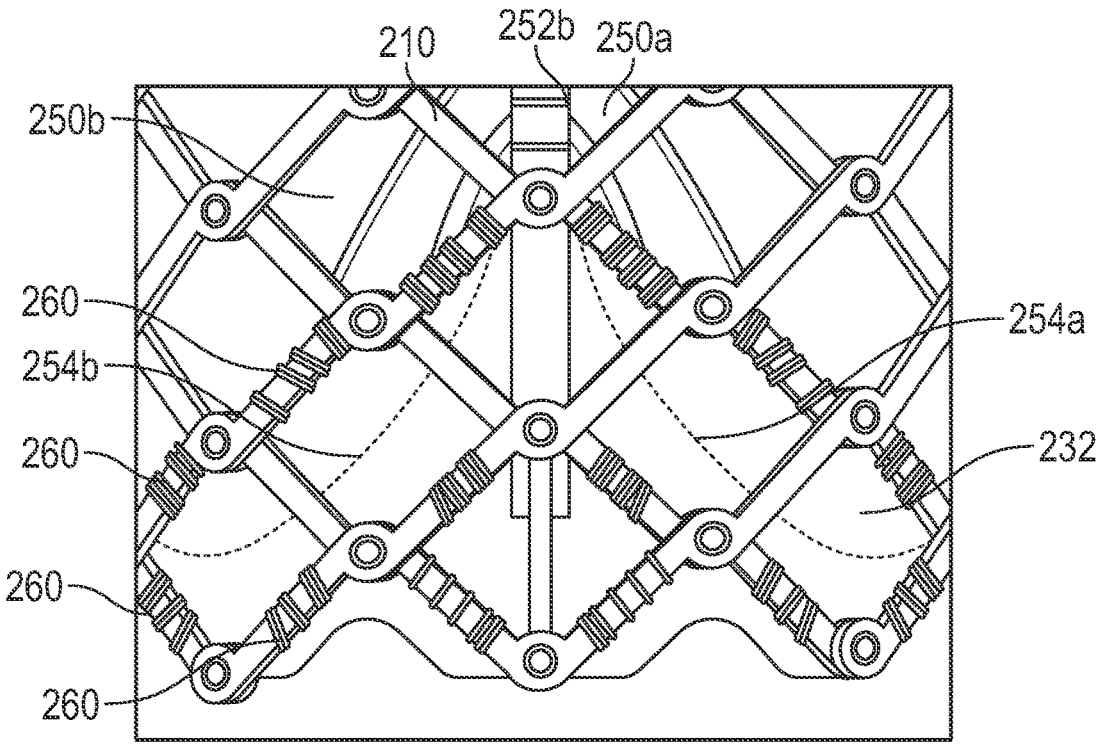
FIGS. 12A and 12B show a portion of a prosthetic heart valve, illustrating coupling of leaflets to the frame.
Figure 12B:
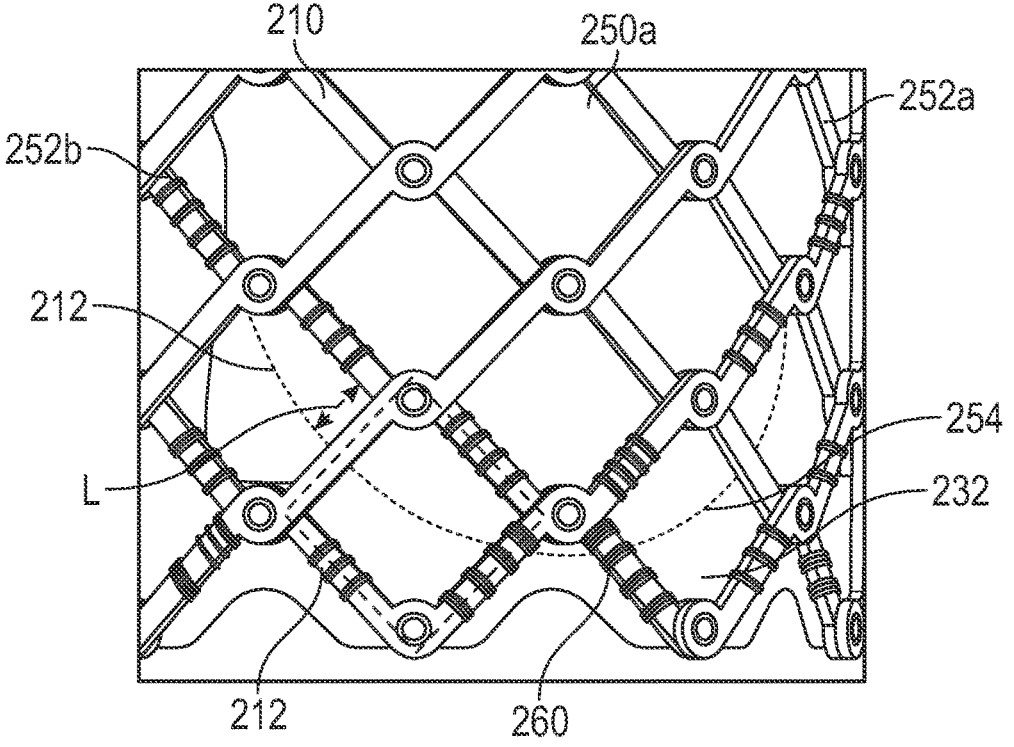

FIGS. 12A-12B show another type of an attachment of leaflets 250 to the frame 210 of a prosthetic valve. FIG. 12A shows two adjacent leaflets 250a and 250b attached to the frame 210. Both leaflets 250a and 250b are attached to a supporting strut of the frame via commissure 252b. FIG. 11B shows the leaflet 250a, attached to the frame at two commissures 252a and 252b. Both leaflets 250a and 250b are sutured to a skirt (having a first cloth 232 and a second cloth 234) via scallop stitch lines 254a and 254b, respectively. The first cloth 232 is shown attached to several different struts 212 both substantially parallel and substantially perpendicular to scallop stitch lines 254a, 254b via suture loops 260.

A varying distance L denotes the distance between the scallop stitch line 254 and the suture loops 260. According to some embodiments, the maximal or average distance L in the embodiments shown if FIGS. 12A-12B is higher than the respective maximal or average distance L of the embodiment shown in FIG. 11. According to some embodiments, the maximal or average distance L in the embodiments shown if FIGS. 12A-12B can be as high as 2 mm.

Figure 13:
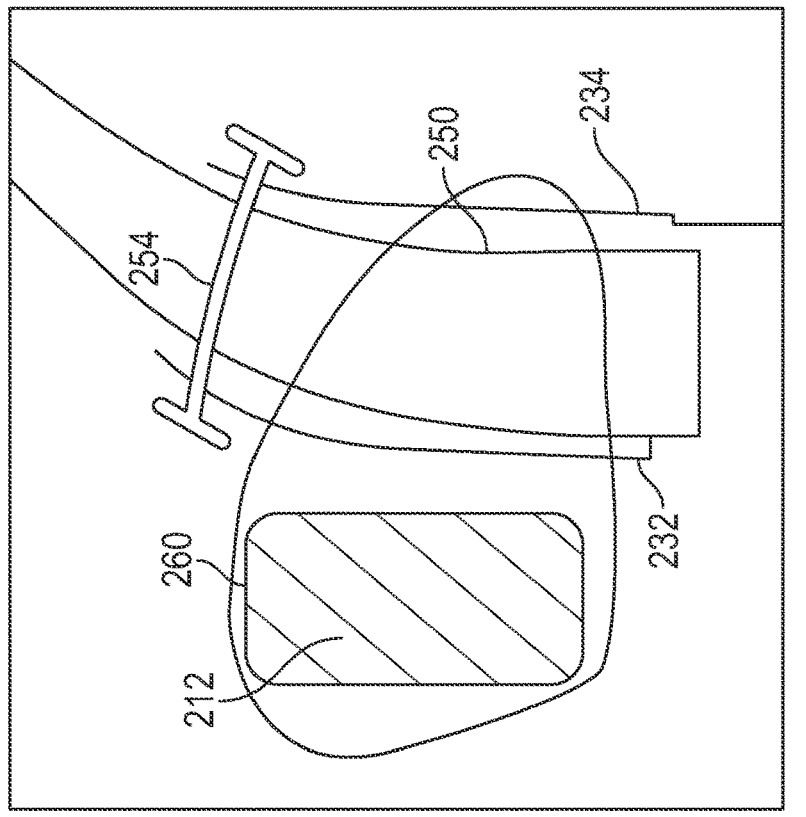
FIG. 13 illustrates coupling a leaflet to a strut using a suture loop that extends around the strut and through the leaflet.

FIG. 13 shows a schematic representation of the attachment of FIG. 11, wherein the first cloth 232 and the second cloth 234 are stitched to both sides of the leaflet 250 via scallop stitch line 254. Suture loop 260 extends through the second cloth 234, the leaflet 250, the first cloth 232, and around the strut 212.

Figure 14:
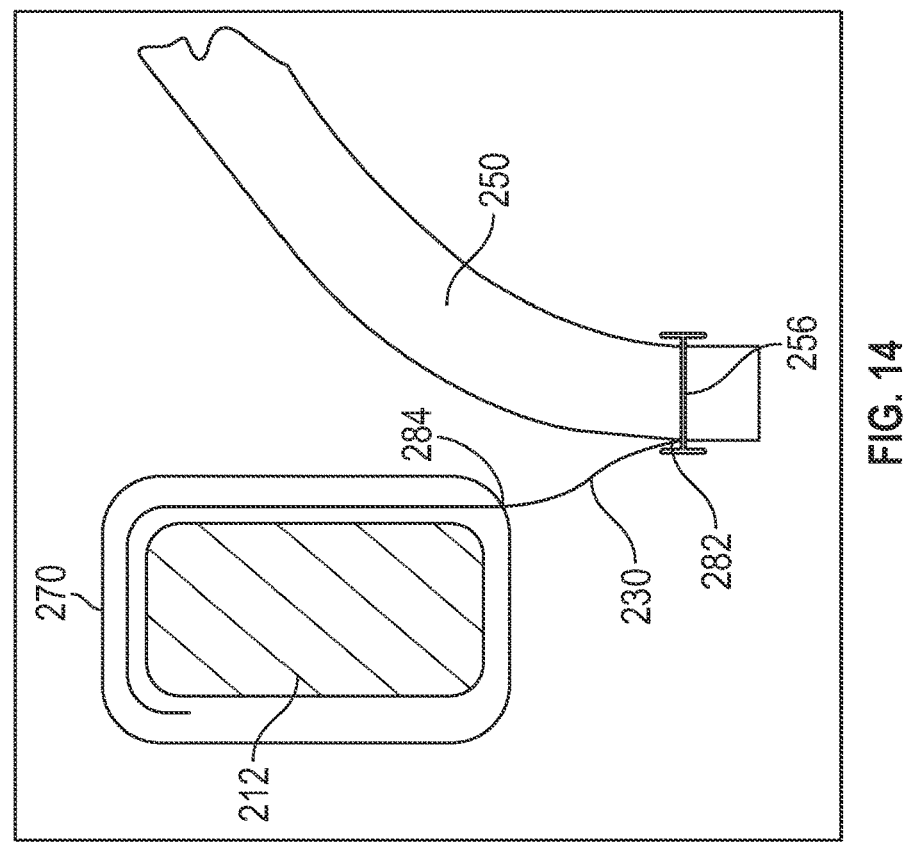
FIG. 14 illustrates coupling a leaflet to a strut using a cloth strip coupled at one end to the strut and coupled and the other end to the leaflet.

An improved mode of attaching a leaflet 250 to struts 212 comprises separately attaching a cloth 230 to the scallop line of a leaflet 250 at one end thereof, and to struts 212 along its opposite end. FIG. 14 shows a schematic representation of an example of such an attachment mode. A cloth strip 230 is stitched to the scallop line of the leaflet 250 via a scallop stitch line 256, similar to the scallop stitch line 254. According to some embodiments, the scallop stitch line 256 extends through stitch holes 282 of the cloth strip 230. The opposite portion of the cloth strip 230 is attached to a strut 212 via a suture loop 270, wherein the suture loop 270 extends only through cloth strip 230, for example through suture holes 284 thereof, and looped around the strut 212, without having the leaflet 250 directly attached to the strut 212. According to some embodiments, the cloth strip 230 is at least partially looped over or covers at least two surfaces of the strut 212 (see example in FIG. 14).

Advantageously, attaching the struts 212 only to the cloth strip 230 via the suture loops 270 is a much simpler process than suturing the suture loops 270 through the leaflet 250 as well, thereby simplifying the attachment process and shortening assembly times, while requiring less skill from an assembler.

Figure 15:
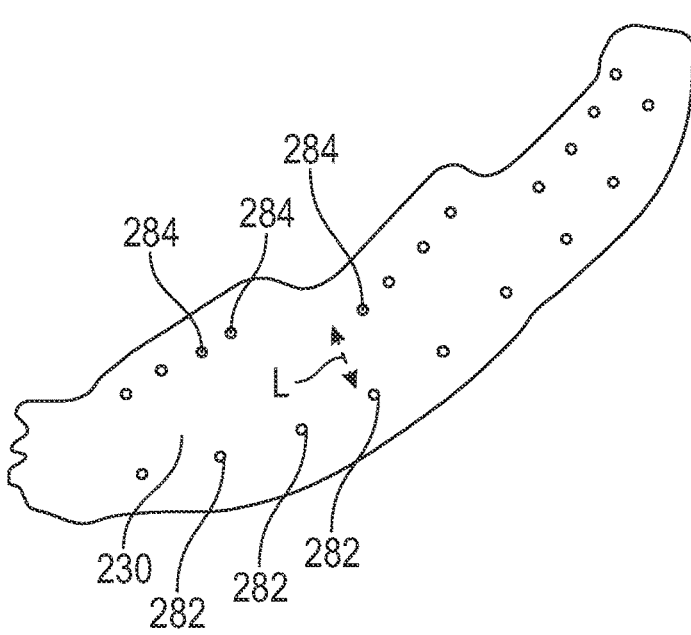
FIG. 15 illustrates a suturing pattern for coupling a leaflet to a strut using a cloth strip.

According to some embodiments, the cloth strip 230 can be provided with a plurality of stitch holes 282 and stitch holes 284, wherein stitch holes 282 are adapted to receive stitch line 256, and stitch holes 284 are adapted to receive suture loops 270, as shown in the example of FIG. 15.

According to some embodiments, stitch holes 284 can be provided in a pattern that matches the strut pattern, such as a zig-zag pattern (see FIG. 15).

Advantageously, providing the cloth 230 with pre-cut stitch holes 282, 284 following the pattern of the struts 212, provides higher accuracy in of attaching the cloth 230 to either the scallop 250 or the struts 212, even when the struts are provided with a challenging geometry.

According to some embodiments, the distance L between the stitch holes 282 and the respective stitch holes 284 is chosen according to a desired distance between the scallop stitch line 256 and the suture loops 270. Advantageously, separating between the suture loops 270 passing through the cloth strip 230 and the scallop stitch line 256 passing through the leaflet 250 provides simpler control over the distance L, for example enabling to design a distance which can be large enough to serve as a shock absorber while providing stress distribution there along, and on the other hand can be short enough to maintain a stable, well positioned infrastructure for the leaflet 250.

A further advantage is that the cloth strip 230 does not act solely as an inner wall skirt portion between the leaflet 250 and the strut 212, but rather as a soft hinge connection.

Preferably, the cloth strip 230 can provide higher stretchability and stress relief during crimping or expansion of the frame 210.

When prosthetic valves are implanted, systolic and diastolic cycles exert forces on the leaflets, which can cause sliding of the leaflet suture loops over the frame strut segments to which they are attached. The oscillating motion of the loops can cause them to lose tension over time, thereby enabling them to more freely slide over the respective strut segment, and may pose the risk of loop abrasion and poor durability.

To avoid this, some embodiments can comprise struts that include tapered strut segments. In such embodiments, some strut segments are tapered such that their width varies between a narrower width at one of the ends of the segment, to a wider width at the opposite end of the segment. Suture loops (or knots) connected to a tapered segment can slide along the segment until their inner diameter matches the corresponding width of the segment. The struts can be assembled together such that their wider ends are oriented towards the inflow of the frame. Preferably, the loops or knots slide along the segments (e.g. towards the inflow) until they are "self-locked" in position, meaning that they are so tightly engages with the segment that any that any further movement there along is prevented. If a loop loses any of its tightness over time, it will slide a little bit further along the segment (e.g. towards the inflow) until it "self-locks" in a new position. Preventing movement of the loops along the segments during systole/diastole cycles mitigates abrasion thereof and improves durability.

Figure 16:
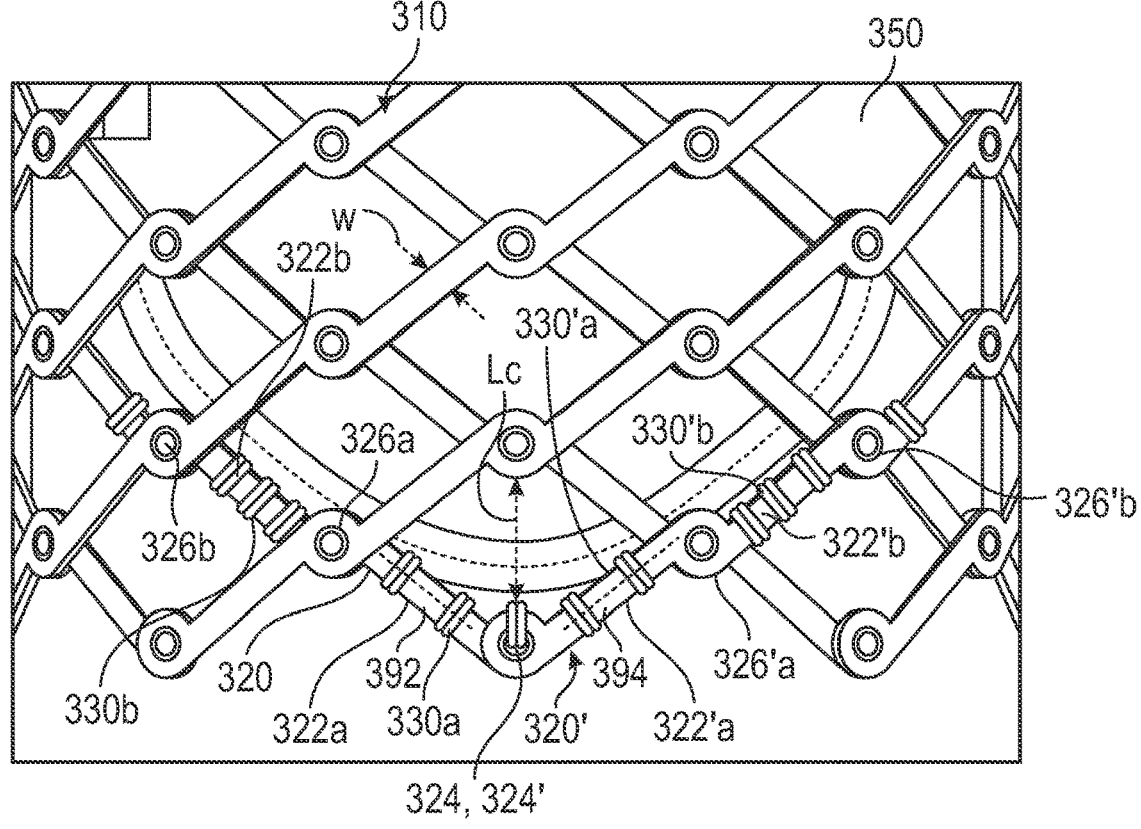
FIG. 16 shows a portion of a prosthetic heart valve, illustrating coupling of a leaflet to the frame.

FIG. 16 shows an attachment of a leaflet 350 to struts 320, 320' of a frame 310 of a prosthetic valve. The leaflets are attached to the frame via two opposing commissures and along its scalloped edge, for example via a skirt or cloth. Attachment to the struts 320, 320' is achieved by a series to suture loops or knots (e.g., 330a, 330b, 330'a, 330'b). The struts 320, 320' include a plurality of segments (e.g., 322a, 322b, 322'a, 322'b) disposed between end portions 324, 324' thereof, and intermediate segments (e.g., 326a, 326b, 326'a, 326'b) disposed between each couple of adjacent segments in a strut. The end portions and the intermediate segments of the struts comprise apertures, through which struts can be connected to each other, for example via fasteners such as pins passing through the apertures, to form junctions. The segments of all of the struts can be provided with uniform width 'w' along their lengths.

In the example of FIG. 16, the leaflet 350 is attached to intersecting struts 320 and 320', connected at their end portions 324, 324' to form an apex. The visible portion of the strut 320 in FIG. 16 comprises a segment 322a extending between end portion 324 and intermediate portion 326a, and a segment 322b extending between the intermediate segment 326a and an intermediate segment 326b. The visible portion of the strut 320' in FIG. 16 comprises a segment 322'a extending between end portion 324' and intermediate portion 326'a, and a segment 322'b extending between the intermediate segment 326'a and an intermediate segment 326'b. The leaflet 350 is attached to the strut 320 via suture loops 330a disposed along the segment 322a, and via suture loops 330b disposed along the segment 322b. Likewise, the leaflet 350 is attached to the strut 320' via suture loops 330'a disposed along the segment 322'a, and via suture loops 330'b disposed along the segment 322'b. Lc denotes the distance between two opposing junctions of a cell of the frame 310, for example between the apex formed by intersecting end portion 324, 324', and the opposing (e.g. vertical) junction (see FIG. 16).

The orientation of the leaflets changes between systole and diastole, wherein forces are exerted by the leaflets during diastole on the suture loops, such that suture loops 330a, 330b tend to slide over segments 322a, 322b, respectively, in direction 392 (i.e. towards an inflow end of the valve), and suture loops 330'a, 330'b tend to slide over segments 322'a, 322'b, respectively, in direction 394. An oscillating motion of the suture loops during systole/diastole cycles poses the risk that the knots of the suture loops will lose tension over time, thereby allowing them to freely slide over the segments of the struts.

Figure 17:
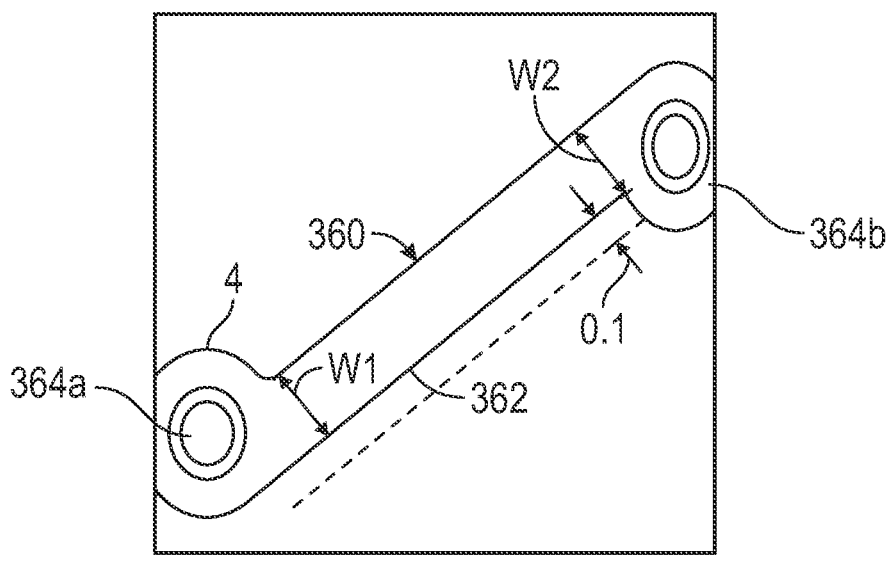
FIGS. 17 and 18 show a frame strut comprising tapered segments.
Figure 18:
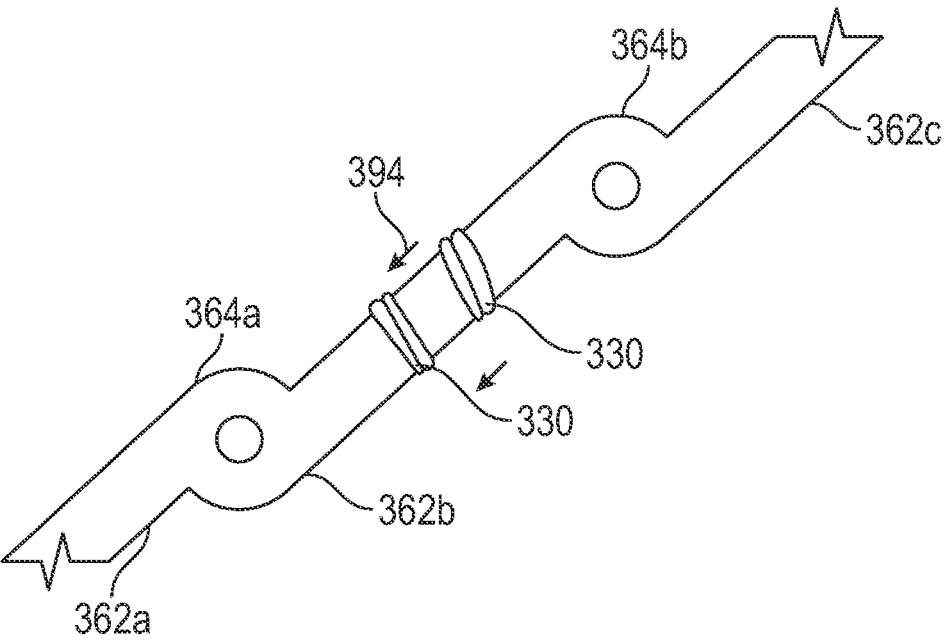

FIG. 17 shows a section of a strut 360 wherein a tapered segment 362 extends between an intermediate segment 364a and an intermediate segment 364b. The tapered segment 362 is provided with a varying width, such that the width W1 at one end thereof, adjacent to the intermediate segment 364a, is greater than the width W2 at the opposite end thereof, adjacent to the intermediate segment 364b. According to some embodiments, all of the segments of a strut 360 are provided as tapered segments 362. FIG. 18 shows a section of the strut 360 with three adjacent tapered segments 362a, 362b and 362c, wherein suture loops 330 are shown knotted over the tapered segment 362b. Suture loops 330 can slide over the tapered segment 362b up to the region wherein their inner diameter matches the segment width. Widening of the segment's width along the region between the suture loop's position and intermediate segment 364a prevents the suture loops 30 from sliding further in the direction 394.

According to some embodiments, the geometry of a strut equipped with tapered segments provides the suture loops with a "self-locking" functionality, wherein each suture loop 330 slides along the segment 362 until it is too tightly engaged with the segment 362 at the corresponding position, preventing any further movement of the suture loop 330 in any direction. If the suture loops losses some of its tension over time, such that its inner diameter expands, it will slide a little but further along the segment and "self-lock" at a new position, having a slightly wider segment width, of the segment 362. Advantageously, the "self-locking" functionality, preventing movement of suture loops 330 along tapered strut segments 362, mitigates abrasion of the loops 330 and improves durability thereof. According to some embodiments, the struts 360 are assembled to form a frame, such that the wider portions of their segment 362 are oriented towards the inflow end of the frame.

When leaflets are attached to frame struts via suture loops that are substantially parallel to their scallop suture lines, while also being attached to the frame via commissures at their opposing lateral ends, changes in frame diameter can result in stretching of the leaflets, accompanied by high stress concentrations along suture loops. One solution to this problem is to have each leaflet attached to struts with suture loops that are substantially perpendicular to the scallop stitch line, via slidable suture loops. However, a problem remains with potential gaps that can form between the scalloped edges of the leaflets and the junctions of frame cells formed along the struts they are attached to, such that the leaflet's edge does not return to its intended position after deployment.

To address this issue, each leaflet can be attached along its scalloped edge to intersecting struts via slidable suture loops. In such embodiments, each pair of suture loops can be attached to sections of intersecting struts, and each suture loop can be slidable over the strut it is attached to, between a distal and a proximal junction thereof. During frame expansion, the suture loops are configured to slide along their respective struts towards the intersecting junction between such struts (specifically, the distal junctions). While the struts are sliding towards the distal junctions, they drag the scallop edge of the leaflet there along in the same direction. This allows the scalloped edge of the leaflets to return to the same position of its expanded, pre-crimped or pre-compressed position.

FIGS. 19A-20B illustrate a technique of attaching leaflets to struts crossing the scallop lines via sliding suture loops.

Figure 19A:
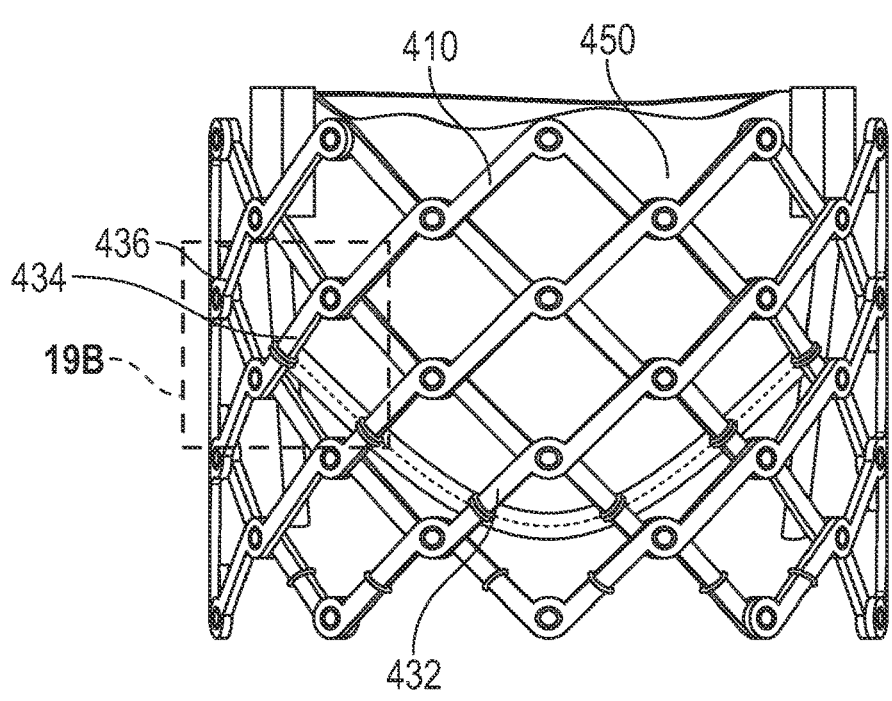
FIG. 19A shows a prosthetic heart valve illustrating coupling of a leaflet to the frame.
Figure 19B:
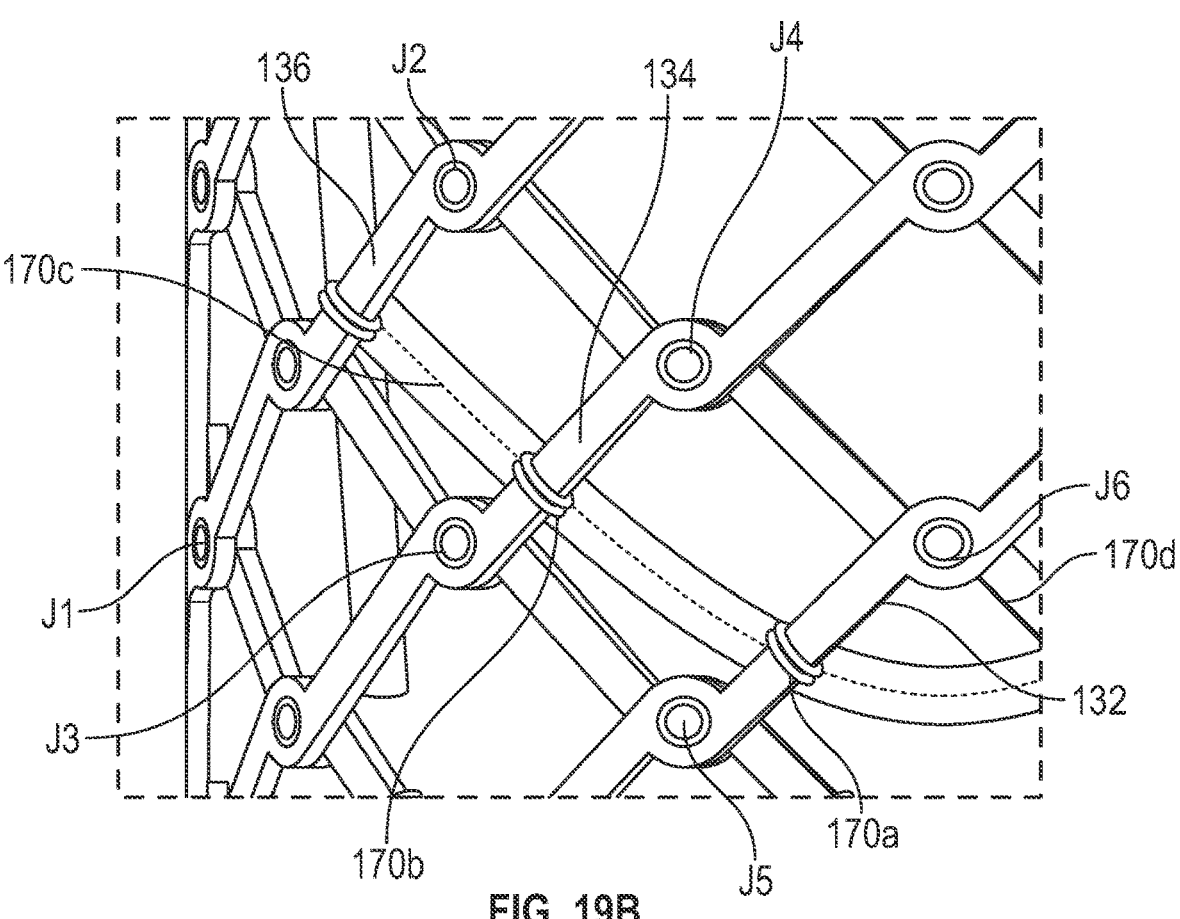
FIG. 19B is an enlarged view of a portion of FIG. 19A.

FIG. 19A shows a leaflet 450 attached to a frame 410. FIG. 19B shows a zoomed in view of region 19B of FIG. 19A. Suture loops 470a, 470b and 470c attach the leaflet 450 to struts 432, 434 and 436, respectively. As shown in FIG. 19B, each suture loop 470 can slide along a respective strut, responding to forces acting there upon as a result of the state and geometry of the frame 410, as well as the structural configuration and attachment regions of the leaflet 450. Suture loop 470a is slidably movable between junctions J5 and J6. Suture loop 470b is slidably movable between junctions J3 and J4. Suture loop 470c is slidably movable between junctions J1 and J2. In FIGS. 19A-19B, while suture loop 470c is positioned closer to one of the junctions, namely J1, suture loops 470b and 470a are positioned closer to the mid-portions between their corresponding junctions.

Figures 20A, 20B:
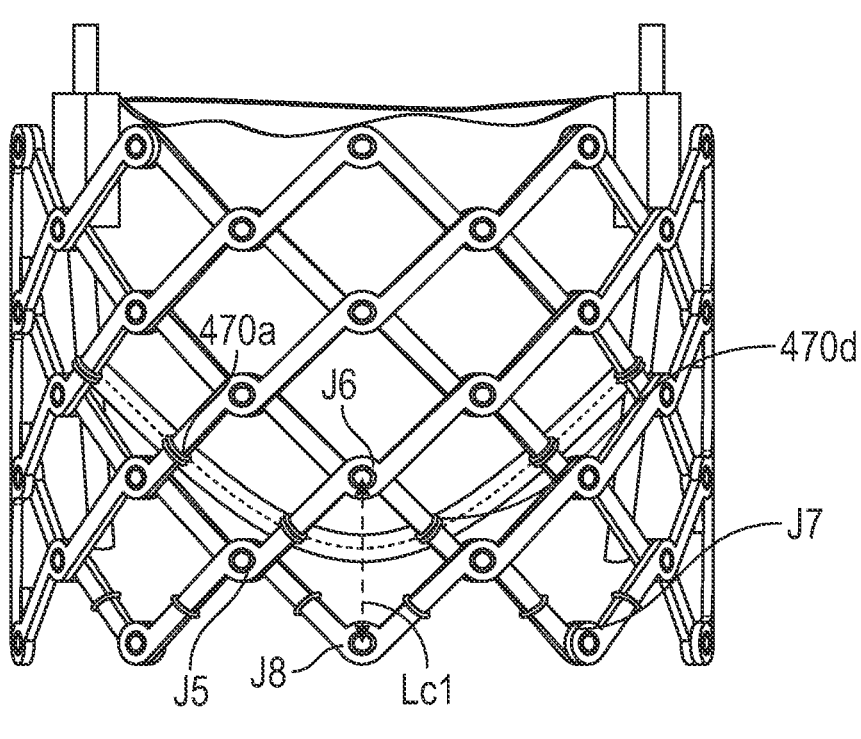
FIGS. 20A and 20B show stages of radial compression of a prosthetic heart valve, illustrating changes in dimensions of frame cells.

FIGS. 20A-20B show two transition stages between a radially expanded frame (FIG. 20A) and a radially slightly compressed frame (FIG. 20B). The longitudinal distance Lc between two opposing junctions of a cell of the frame is increasing from Lc1 to Lc2, such that Lc1<Lc2. Suture loop 470a is slidably movable between junction J5 and J6, and suture loop 470b is slidably movable between junctions J7 and J6. The position of the suture loops 470a and 470b changes along the struts between their respective junctions according to the changing frame diameter, such that the scalloped edge of the leaflet is displaced toward junction J6 and away from junction J8 as the frame is further compressed to a fully crimped state (not shown), forming a gap between the scalloped edge of the leaflet and junction J8.

Figure 21A:
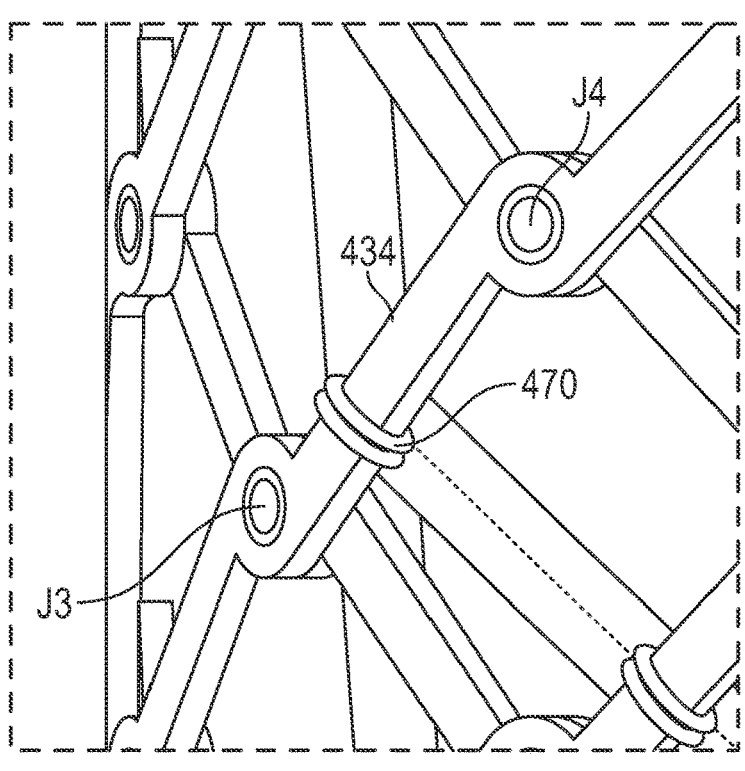
FIGS. 21A and 21B illustrate coupling of a leaflet to a frame with suture loops, illustrating how the suture loops can slide along the strut segments.
Figure 21B:
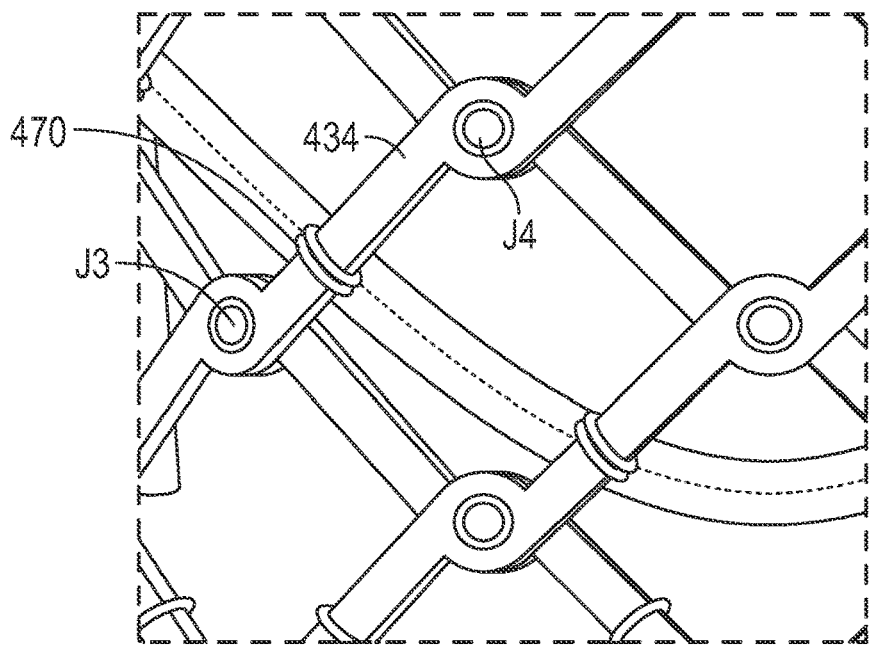

FIG. 21A is an enlarged view of the position of a suture loop 470 at a pre-crimped expanded state of the frame, wherein the suture loop 470 is adjacent to the junction J3. FIG. 21B is an enlarged view of the position of a suture loop 470 after valve-crimping followed by frame expansion. When the frame is crimped the suture loops 470 tend to slide towards the junctions closer to the outflow of the valve (i.e. towards junction J4 in the illustrated example). Once the frame is expanded from the crimped state, as demonstrated in FIG. 21B, the suture loops do not return to the original position of FIG. 21A, but are rather spaced farther away from the junction J3, such that the scalloped edge of the leaflets are positioned closer to the outflow of the valve, relative to their pre-crimped original position.

Figure 22A:
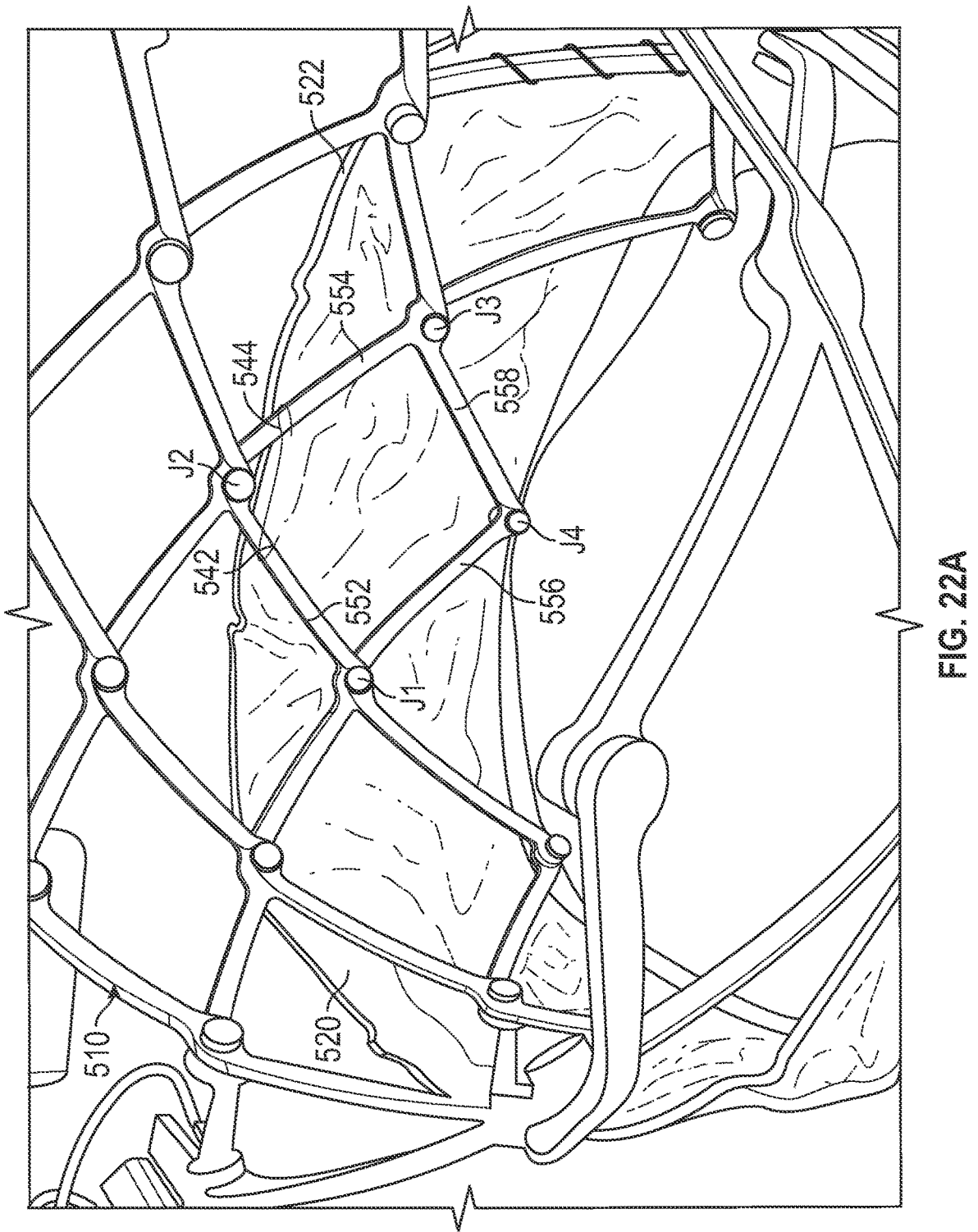
FIG. 22A shows an internal view of a prosthetic heart valve illustrating coupling of a leaflet to the frame.
Figure 22B:
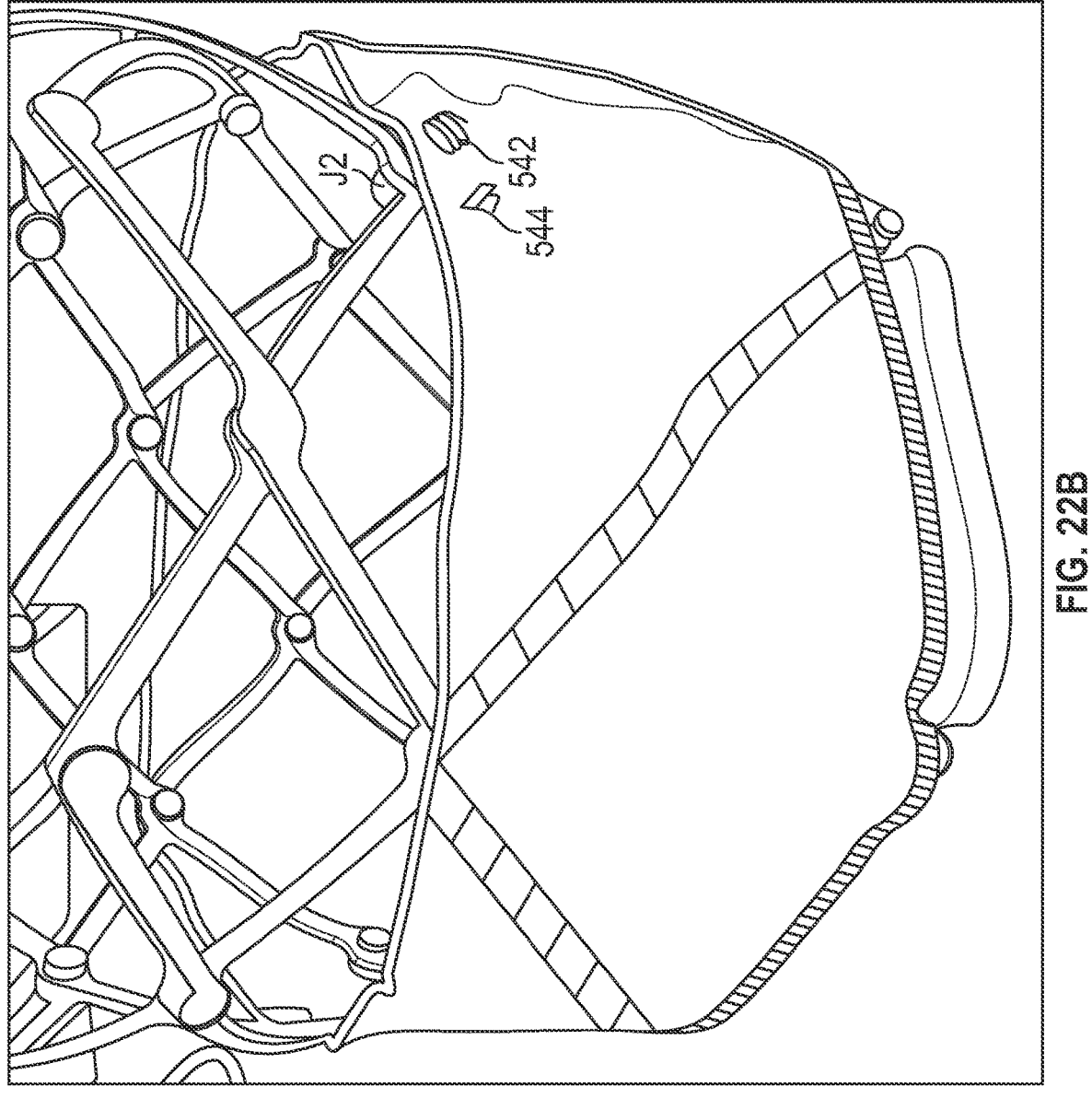
FIG. 22B shows an external view of the prosthetic heart valve of FIG. 22A.

FIGS. 22A-23D illustrate an attachment configuration of a skirt to a frame of a prosthetic valve, wherein the attachment configuration is configured to assist in returning the scalloped edge of the leaflet to its pre-crimped state upon expansion, such as demonstrated in FIG. 21BA. FIGS. 22A and 22B show a frame 510 of a prosthetic valve, having a skirt 520 attached to struts thereof. FIGS. 22A and 22B show the attachment of the skirt 520 to the frame 510 from an internal view angle and an external view angle, respectively, of the frame 510. The skirt 520 is attached to intersecting struts via suture loops. FIG. 22A shows two such suture loops 542 and 544, attaching a section of the skirt 520 to struts 552 and 554, respectively. The suture loops can be connected via a string (not numbered separately), and can form the end portions of the string, sutured to two crossing struts. The struts 552 and 554 constitute two edges of one cell of the frame 510, intersecting at a junction point J2. The suture loops are not attached too tightly to the struts, but rather are loose enough so as to enable them to slide along the respective struts. The suture loop 542 is slidably movable along the strut 552 between junctions J1 and J2. The suture loop 544 is slidably movable along the strut 554 between junctions J3 and J2.

Figure 23B:
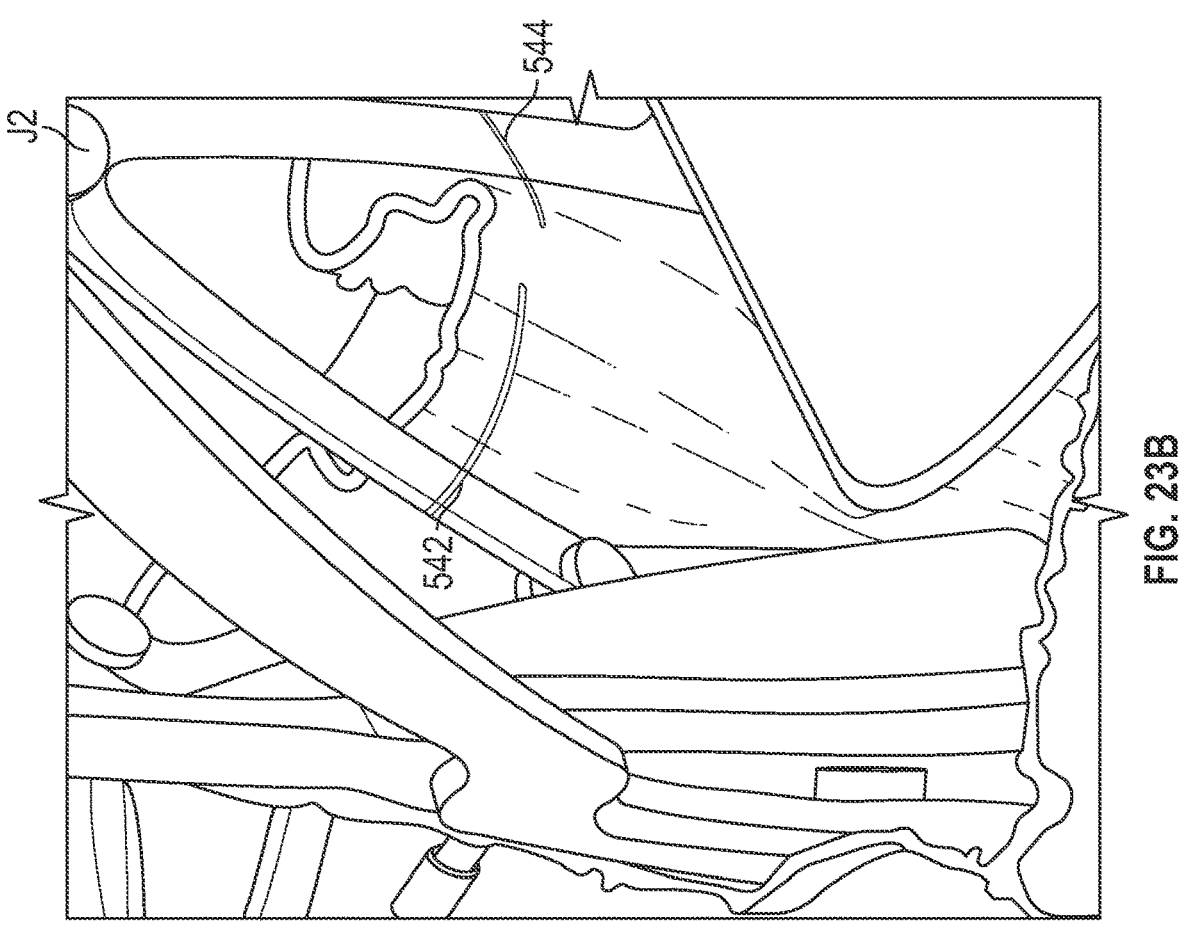
FIGS. 23A-23D illustrate further techniques for suturing leaflets and other materials to the inside of a frame.
Figure 23A:
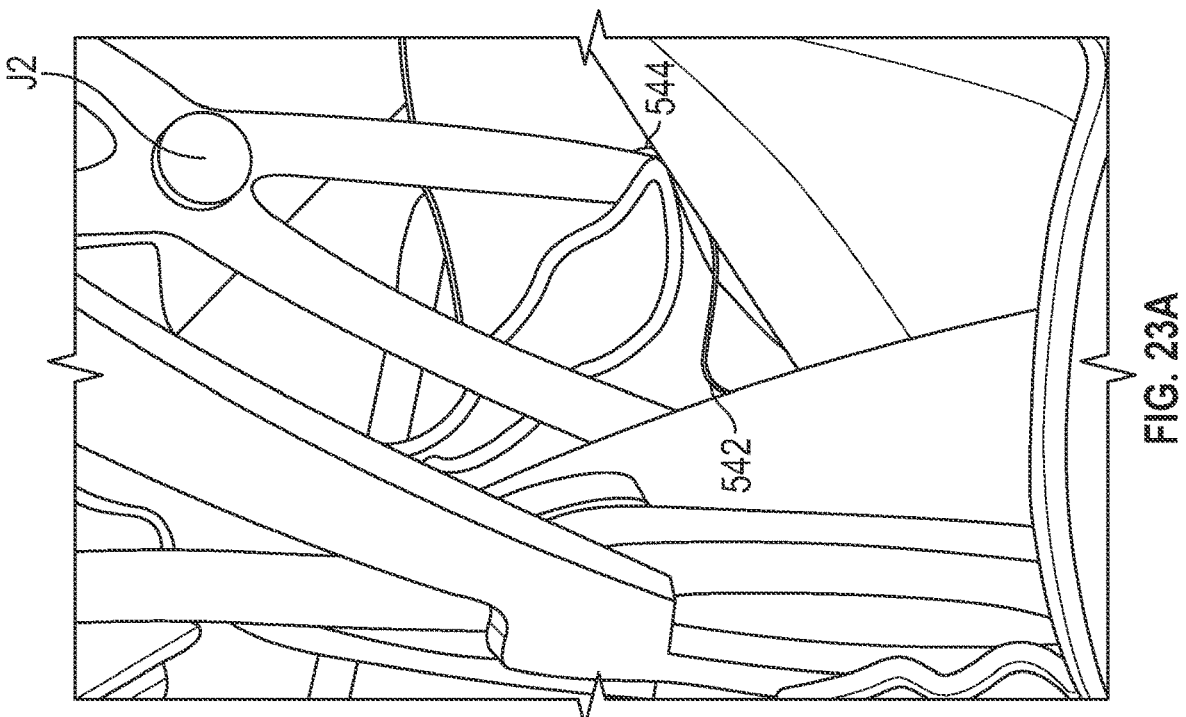
Figure 23D:
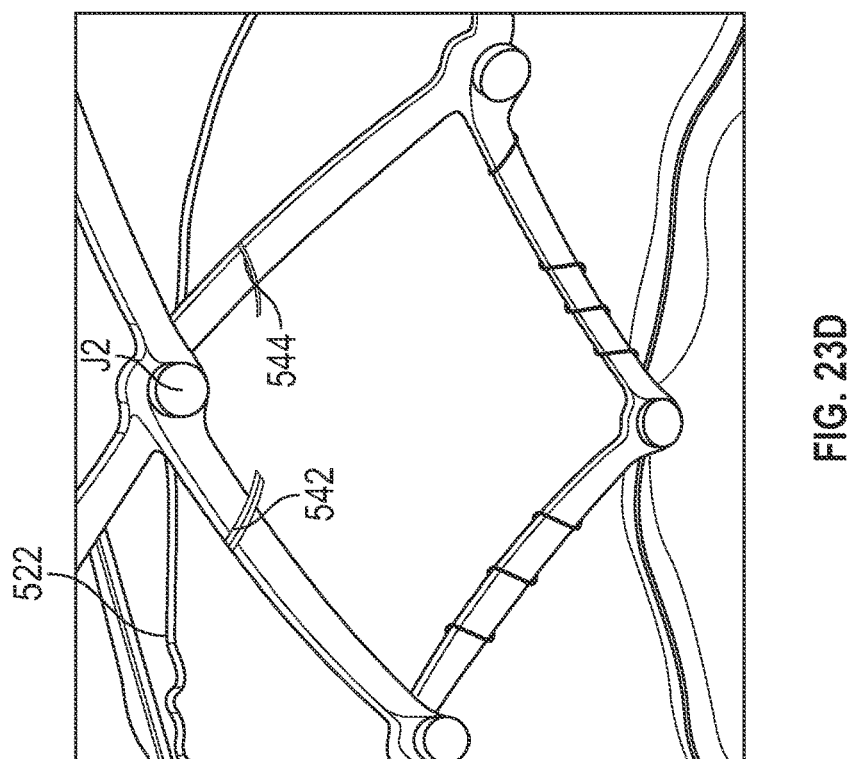
Figure 23C:
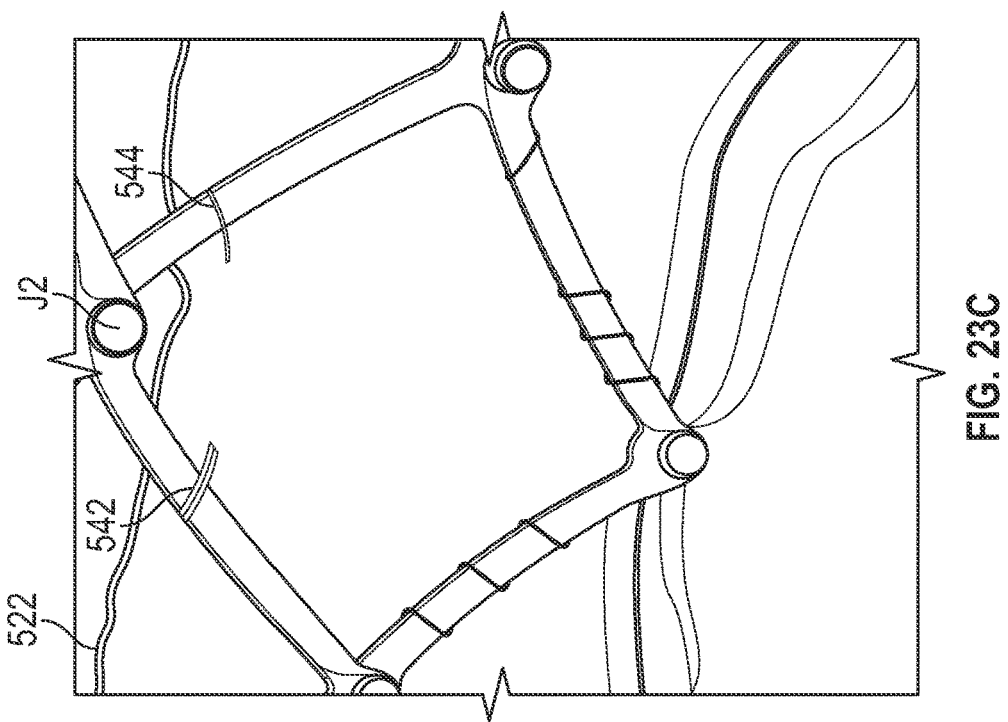

FIGS. 23A-23D show different transition stages between a radially compressed frame (FIG. 23A) and a radially expanded frame (FIG. 23D). Suture loops 542 and 544 are slidably movable along the respective struts they are attached to, such that their position changes according to the changing frame diameter. It can be appreciated that as the frame expands, the suture loops 542 and 544 slide towards the intersecting junction J2 between their respective struts, dragging the skirt edge 522 there along. Specifically, while the skirt edge 522 is shown to be distanced away from the junction J2 when the frame is compressed (FIG. 22A), for example—during a crimped stage, it is aligned therewith at the expanded state (FIG. 23D), preventing gap formation between the junction J2 and the skirt edge 522.

Figure 24:
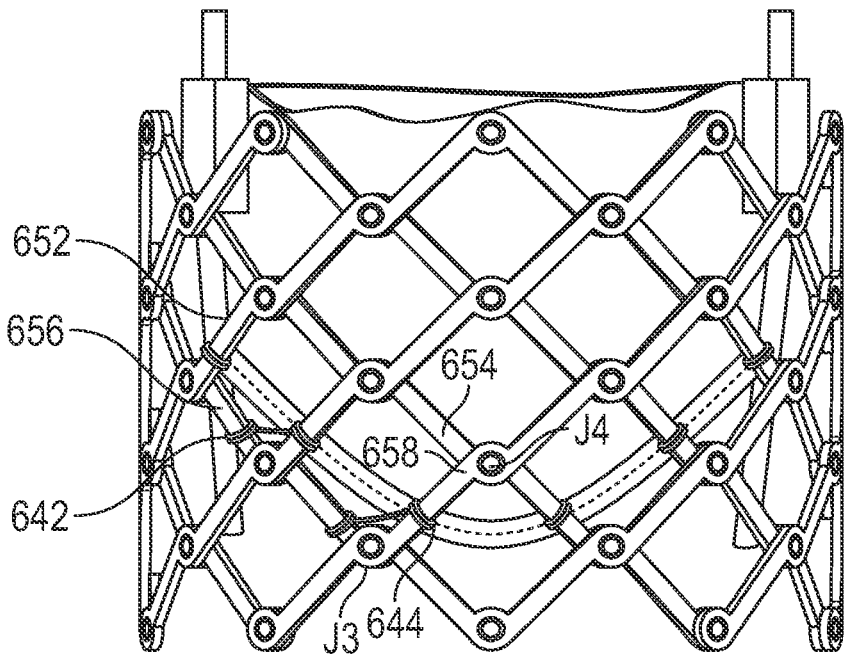
FIG. 24 shows a prosthetic heart valve illustrating coupling of a leaflet to the frame.

According to an aspect of this technology, there is provided a method of attaching each leaflet of a prosthetic valve along its scalloped edge to intersecting struts via slidable suture loops. A prosthetic valve can include a plurality of leaflets (not shown in the figures) each being attached to the frame via two opposing commissures, and along, or in the vicinity of, its scalloped edge. FIG. 24 shows suture loops 642 and 644 attached to the leaflet. As can be seen, contrary to the attachment regions shown in FIG. 22A for the skirt 520, suture loops 642 and 644 are slidably movable along the struts opposing those of the struts utilized in FIG. 22A in each cell. Specifically, suture loops 642 and 644, are attached to and slidably movable along the struts 656 and 658, instead of struts 652 and 654 that might have been utilized for skirt attachment. Suture loops 642 and 644 are similar in structure and function to suture loops 542 and 544. For example, suture loop 644 is slidably movable along the strut 658 between junctions J3 and J4.

As the frame expands, the suture loops 442 and 444 are configured to slide towards the intersecting junction J3 between their respective struts 656 and 656, dragging the scallop edge of the leaflet there along. Specifically, while the scallop edge will be distanced away from the junction J3 when the frame is compressed, it will align therewith at the expanded state, preventing gap formation between the junction J3 and the scallop edge of the leaflet, similar to the pre-crimped position of FIG. 21A.

A significant advantage of the disclosed technology is that it allows the use of a sliding scallop line during the crimping phase (as shown in FIGS. 19A-20B), while making certain that the leaflets' scallop lines are positioned correctly after deployment.

General Considerations

The herein disclosed embodiments can be adapted for delivering and implanting prosthetic devices in any of the native annuluses of the heart (e.g., the aortic, pulmonary, mitral, and tricuspid annuluses), and can be used with any of various delivery devices for delivering the prosthetic valve using any of various delivery approaches (e.g., retrograde, antegrade, transseptal, transventricular, transatrial, etc.). The prosthetic heart valves can be radially collapsed during delivery through the body and then radially expanded at the implantation site, such as by using a delivery device coupled to the valve. The valves and other implantable devices disclosed herein can be delivered using a catheter and/or a guidewire. A guidewire can be advanced through the patient and then a catheter can be advanced over the guidewire. The catheter can have an innermost shaft that defines a guidewire lumen, through which the guidewire passes. The catheter can be part of a delivery system, which may also include more than one catheter, shaft, and/or sheath, actuation mechanisms, power mechanisms, and other components. For example, the delivery device can include an actuation mechanism that mechanically expands the frame at the implantation site.

For purposes of this description, certain aspects, advantages, and novel features of the embodiments of this disclosure are described herein. The disclosed methods, apparatus, and systems should not be construed as being limiting in any way. Instead, the present disclosure is directed toward all novel and nonobvious features and aspects of the various disclosed embodiments, alone and in various combinations and sub-combinations with one another. The methods, apparatus, and systems are not limited to any specific aspect or feature or combination thereof, nor do the disclosed embodiments require that any one or more specific advantages be present or problems be solved. The technologies from any example can be combined with the technologies described in any one or more of the other examples. In view of the many possible embodiments to which the principles of the disclosed technology may be applied, it should be recognized that the illustrated embodiments are only preferred examples and should not be taken as limiting the scope of the disclosed technology.

Although the operations of some of the disclosed embodiments are described in a particular, sequential order for convenient presentation, it should be understood that this manner of description encompasses rearrangement, unless a particular ordering is required by specific language set forth herein. For example, operations described sequentially may in some cases be rearranged or performed concurrently. Moreover, for the sake of simplicity, the attached figures may not show the various ways in which the disclosed methods can be used in conjunction with other methods. Additionally, the description sometimes uses terms like "provide" or "achieve" to describe the disclosed methods. These terms are high-level abstractions of the actual operations that are performed. The actual operations that correspond to these terms may vary depending on the particular implementation and are readily discernible by one of ordinary skill in the art.

As used in this application and in the claims, the singular forms "a," "an," and "the" include the plural forms unless the context clearly dictates otherwise. Additionally, the term "includes" means "comprises." As used herein, "and/or" means "and" or "or", as well as "and" and "or". Further, the terms "coupled" and "connected" generally mean physically (e.g., mechanically or chemically), electrically, and/or magnetically coupled or linked and does not exclude the presence of intermediate elements between the coupled or associated items absent specific contrary language.

Directions and other relative references (e.g., inner, outer, upper, lower, etc.) may be used to facilitate discussion of the drawings and principles herein, but are not intended to be limiting. For example, certain terms may be used such as "inside," "outside,", "top," "down," "interior," "exterior," and the like. Such terms are used, where applicable, to provide some clarity of description when dealing with relative relationships, particularly with respect to the illustrated embodiments. Such terms are not, however, intended to imply absolute relationships, positions, and/or orientations. For example, with respect to an object, an "upper" part can become a "lower" part simply by turning the object over. Nevertheless, it is still the same part and the object remains the same.

The valves and frames disclosed herein are described using an axial direction defined by the centerline of the annular frame and the overall blood flow direction from an inflow end to an outflow end, a radial direction that is defined as radiating perpendicularly from the centerline of the frame, and a circumferential direction that is perpendicular to the axial and radial directions and extends around the centerline of the frame. The term "inner" refers to objects, surfaces and areas proximal to the centerline of the frame and the term "outer" refers objects, surfaces and areas that are farther from the centerline of the frame.

In view of the many possible embodiments to which the principles of the disclosed technology may be applied, it should be recognized that the illustrated embodiments are only preferred examples of the technology and should not be taken as limiting the scope of the technology. Rather, the scope of the disclosed technology is at least as broad as the following claims and their equivalents.

The invention claimed is:

1. A prosthetic heart valve comprising:
a radially expandable and collapsible annular frame comprising a plurality of intersecting struts coupled together at pivot joints, wherein radial expansion or contraction of the annular frame causes the intersecting struts to pivot relative to one another at the pivot joints; and
a valvular structure mounted within the frame that regulates blood flow through the prosthetic heart valve, the valvular structure comprising leaflets;
wherein the leaflets are coupled to the frame at lateral commissure ends of the leaflets and along scalloped edges of the leaflets that extend between the lateral commissure ends; and
wherein the scalloped edges of the leaflets are coupled to segments of the struts of the frame via suture loops, and the strut segments to which the suture loops are coupled are oriented transverse to the scalloped edges of the leaflets.

2. The valve of claim 1, wherein the coupling of the scalloped edges of the leaflets to strut segments that are oriented transverse to the scalloped edges allows movement of the scalloped edges relative to the strut segments via the suture loops sliding along the strut segments during radial expansion and compression of the frame.

3. The valve of claim 1, wherein during systole and diastole, anatomical forces acting on the leaflets at attachment points to the struts along the scalloped edges is substantially perpendicular to the suture loops, thereby inhibiting undesirable abrasion of the suture loops and the leaflets.

4. The valve of claim 1, wherein the scalloped edge of each leaflet is coupled via suture loops to segments of at least six different struts of the frame; and
wherein the at least six different struts comprises three parallel strut segments on one side of the scalloped edge and another three parallel strut segments on a second side of the scalloped edge.

5. The valve of claim 1, wherein the strut segments to which the suture loops are coupled are oriented substantially perpendicular to the scalloped edges of the leaflets.

6. The valve of claim 1, wherein each of the struts of the frame is pivotably coupled to three or more other struts of the frame at respective mechanical pivot joints, such that the struts can pivot relative to one another without deforming; and
wherein each strut comprises at least three strut segments, with each strut segment extending between two adjacent mechanical pivot joints.

7. The valve of claim 1, wherein the strut segments are tapered such that they reduce in width from an inflow end of the frame toward an outflow end of the frame;

wherein the leaflets are coupled to the tapered strut segments via suture loops that extend around the tapered strut segments, such that the suture loops are large enough to fit around narrower ends of the tapered strut segments and small enough to not fit around wider ends of the tapered strut segments; and wherein the suture loops are configured to slide along the tapered strut segments from the narrower ends toward the wider ends and become frictionally self-locked at an intermediate location along the tapered strut segments where the suture loops are equal in circumference to the strut segments.

8. A prosthetic heart valve comprising:

a radially expandable and collapsible annular frame comprising a plurality of intersecting struts coupled together at pivot joints, wherein radial expansion or contraction of the annular frame causes the intersecting struts to pivot relative to one another at the pivot joints; and a valvular structure mounted within the frame that regulates blood flow through the prosthetic heart valve, the valvular structure comprising three leaflets; and a scallop line infrastructure that comprises three scallop line elements, with each of the three scallop line elements being attached to a scalloped edge of a respective one of the three leaflets;

wherein each of the scallop line elements comprises two opposing end portions and a central portion between the two opposing end portions, wherein the end portions are attached to the frame along with lateral ends of the leaflets at commissures, and wherein the central portions of the scallop line elements are attached to the scalloped edges of the leaflets and are free of the frame;

wherein the scalloped edges of the leaflets are coupled to segments of the struts of the frame via suture loops, and the strut segments to which the suture loops are coupled are oriented transverse to the scalloped edges of the leaflets.

9. The valve of claim 8, wherein the scallop line elements are formed of a rigid material, selected from the group consisting of a metal and a metal alloy and are resiliently deformable to resist radially inward displacement of the scalloped edges of the leaflets.

10. The valve of claim 8, wherein the scallop line elements are formed of a soft material selected from the group consisting of a short skirt, cloth, and string.

11. The valve of claim 8, wherein the scallop line elements are flexible to allow the central portions of the scallop line elements to deform from a generally U shape to a generally V shape during radial compression of the frame while the end portions of the scallop line elements move toward each other.

12. The valve of claim 8, wherein each of the struts of the frame is pivotally coupled to three or more other struts of the frame at respective mechanical pivot joints, such that the struts can pivot relative to one another without deforming; and wherein each strut comprises at least three strut segments, with each strut segment extending between two adjacent mechanical pivot joints.

13. The valve of claim 8, wherein the strut segments are tapered such that they reduce in width from an inflow end of the frame toward an outflow end of the frame;

wherein the leaflets are coupled to the tapered strut segments via suture loops that extend around the tapered strut segments, such that the suture loops are large enough to fit around narrower ends of the tapered strut segments and small enough to not fit around wider ends of the tapered strut segments; and wherein the suture loops are configured to slide along the tapered strut segments from the narrower ends toward the wider ends and become frictionally self-locked at an intermediate location along the tapered strut segments where the suture loops are equal in circumference to the strut segments.

14. The valve of claim 8, wherein the central portions of the scallop line elements extend between two adjacent strut segments of two intersecting struts.

15. A prosthetic heart valve comprising:

a radially expandable and collapsible annular frame comprising a plurality of intersecting struts coupled together at pivot joints, wherein radial expansion or contraction of the annular frame causes the intersecting struts to pivot relative to one another at the pivot joints, and wherein the struts of the frame comprise plural strut segments between the pivot joints; and a valvular structure mounted within the frame that regulates blood flow through the prosthetic heart valve, the valvular structure comprising plural leaflets that each have commissure ends and scalloped edges extending between the commissure ends;

wherein each scalloped edge is coupled to adjacent segments of intersecting struts via sliding suture loops, the adjacent segments joining at a common pivot joint of the pivot joints, wherein the sliding suture loops are permitted to slide along the adjacent segments both toward and away from the common pivot joint.

16. The valve of claim 15, wherein during radial frame expansion, the sliding suture loops slide along the adjacent segments toward the common pivot joint.

17. The valve of claim 15, wherein during radial frame contraction, the sliding suture loops slide along the adjacent segments away from the common pivot joint.

18. The valve of claim 15, wherein each of the struts of the frame is pivotally coupled to three or more other struts of the frame at respective mechanical pivot joints, such that the struts can pivot relative to one another without deforming; and wherein each strut comprises at least three strut segments, with each strut segment extending between two adjacent mechanical pivot joints.

19. The valve of claim 15, wherein the strut segments are tapered such that they reduce in width from an inflow end of the frame toward an outflow end of the frame;

wherein the leaflets are coupled to the tapered strut segments via suture loops that extend around the tapered strut segments, such that the suture loops are large enough to fit around narrower ends of the tapered strut segments and small enough to not fit around wider ends of the tapered strut segments; and wherein the suture loops are configured to slide along the tapered strut segments from the narrower ends toward the wider ends and become frictionally self-locked at an intermediate location along the tapered strut segments where the suture loops are equal in circumference to the strut segments.

20. The valve of claim 15, further comprising a scallop line infrastructure that comprises three scallop line elements, with each of the three scallop line elements being attached to a scalloped edge of a respective one of the leaflets.

*    *    *    *    *